(12) United States Patent
Thompson et al.

(10) Patent No.: US 10,194,808 B1
(45) Date of Patent: Feb. 5, 2019

(54) CORRELATED HEMODYNAMIC MEASUREMENTS

(71) Applicant: Verily Life Sciences LLC, Mountain View, CA (US)

(72) Inventors: Jason Donald Thompson, Palo Alto, CA (US); Andrew Homyk, Belmont, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 363 days.

(21) Appl. No.: 14/583,861

(22) Filed: Dec. 29, 2014

(51) Int. Cl.
| | |
|---|---|
| A61B 5/02 | (2006.01) |
| A61B 5/026 | (2006.01) |
| A61B 5/021 | (2006.01) |
| A61B 5/024 | (2006.01) |
| A61B 5/0402 | (2006.01) |
| A61B 5/145 | (2006.01) |
| A61B 5/00 | (2006.01) |
| A61B 8/08 | (2006.01) |

(52) U.S. Cl.
CPC ........ *A61B 5/02028* (2013.01); *A61B 5/0059* (2013.01); *A61B 5/021* (2013.01); *A61B 5/024* (2013.01); *A61B 5/026* (2013.01); *A61B 5/02007* (2013.01); *A61B 5/0402* (2013.01); *A61B 5/14542* (2013.01); *A61B 5/6824* (2013.01); *A61B 5/7285* (2013.01); *A61B 8/488* (2013.01)

(58) Field of Classification Search
USPC .................................................. 600/300–301
See application file for complete search history.

(56) References Cited

U.S. PATENT DOCUMENTS

| | | | |
|---|---|---|---|
| 2011/0169978 A1* | 7/2011 | Lasser | A61B 3/1233 348/222.1 |
| 2011/0190601 A1* | 8/2011 | Osypka | A61B 5/02007 600/301 |
| 2012/0019690 A1* | 1/2012 | Stirling-Gallacher | G01S 7/2923 348/241 |
| 2012/0053433 A1* | 3/2012 | Chamoun | A61B 5/0261 600/324 |
| 2012/0203077 A1* | 8/2012 | He | A61B 5/02055 600/301 |

(Continued)

*Primary Examiner* — Carl H Layno
*Assistant Examiner* — Dacheng Xie
(74) *Attorney, Agent, or Firm* — McDonnell Boehnen Hulbert & Berghoff LLP

(57) ABSTRACT

Wearable devices are described herein including at least two sensors configured to detect hemodynamic properties of a wearer. A first sensor is configured to detect a hemodynamic property of a portion of vasculature, where the operation of the first sensor is based on a hemodynamic property detected by a second sensor. A timing of operation, a value of one or more controlled operational parameters, a filter setting, or some other aspect of the operation of the first sensor could be controlled based on the hemodynamic property detected by the second sensor. Hemodynamic properties could include blood flow rate, volume, and/or pressure in one or more portions of vasculature, a timing, rate, delay, or other information about heartbeats, an oxygenation level of blood, a velocity of blood cells in blood, or some other information about a wearer's blood, heart, and/or cardiovascular system.

18 Claims, 9 Drawing Sheets

(56) References Cited

U.S. PATENT DOCUMENTS

| | | |
|---|---|---|
| 2013/0060480 A1* | 3/2013 | Korhonen ............ A61B 5/1118 |
| | | 702/19 |
| 2013/0245456 A1* | 9/2013 | Ferguson, Jr. ....... A61B 5/0059 |
| | | 600/473 |
| 2014/0051939 A1 | 2/2014 | Messerschmidt |
| 2014/0051941 A1 | 2/2014 | Messerschmidt |
| 2014/0094675 A1 | 4/2014 | Luna et al. |
| 2014/0249443 A1 | 9/2014 | Banet et al. |
| 2014/0257049 A1* | 9/2014 | Soundarapandian .. A61B 5/681 |
| | | 600/301 |
| 2014/0275854 A1* | 9/2014 | Venkatraman ......... A61B 5/721 |
| | | 600/301 |
| 2014/0276123 A1* | 9/2014 | Yang ................... A61B 5/7275 |
| | | 600/483 |

* cited by examiner

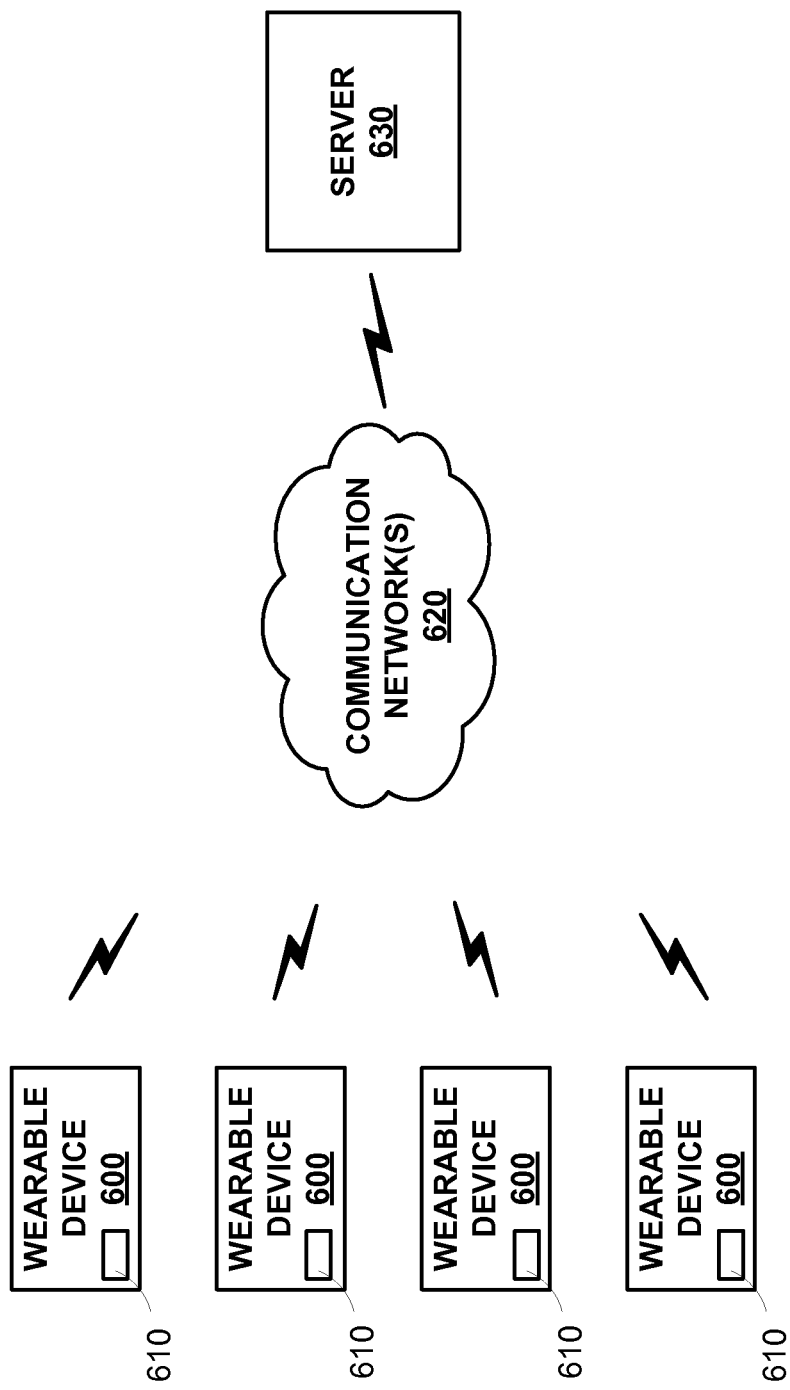

CORRELATED HEMODYNAMIC MEASUREMENTS

BACKGROUND

Unless otherwise indicated herein, the materials described in this section are not prior art to the claims in this application and are not admitted to be prior art by inclusion in this section.

Certain medical states or conditions of a human body can be detected using sensors disposed outside of the human body (e.g., disposed against, on, or otherwise proximate an external body surface of the human body). Some medical states or conditions can change slowly, occur rarely, or have other properties otherwise indicating that monitoring of the human body over an extended period of time is preferred. Sensors disposed in a wearable device can enable long-term monitoring of a medical state or condition of the body of a wearer while allowing the wearer to perform activities of daily living, to travel, to commute, or to engage in other activities with minimal interruption. Such monitoring by a wearable device could be performed preventatively, e.g., to monitor an otherwise healthy wearer's health state over time to enable early detection of an adverse medical condition, to develop data describing a 'healthy' baseline state of the wearer, or to enable other applications. Medical states or conditions of a human body monitored by such a wearable device can include pulse rate, blood oxygenation, activity level, blood pressure, galvanic skin response, or other information about the body of a wearer.

SUMMARY

Some embodiments of the present disclosure provide a wearable device including: (i) a first sensor, wherein the first sensor is configured to detect a first hemodynamic property relating to a first portion of subsurface vasculature of a wearer of the wearable device; (ii) a second sensor configured to detect a second hemodynamic property relating to a wearer of the wearable device; (iii) a mount configured to mount the first sensor and the second sensor to an external body surface of the wearer such that the first sensor is proximate to the first portion of subsurface vasculature; and (iv) a controller operably coupled to the first and second sensors, wherein the controller includes a computing device programmed to perform operations including: (a) detecting, using the second sensor, the second hemodynamic property relating to the wearer; and (b) detecting, using the first sensor, the first hemodynamic property relating to the first portion of subsurface vasculature, wherein using the first sensor to detect the first hemodynamic property of the first portion of subsurface vasculature includes operating the first sensor based at least on the second hemodynamic property detected using the second sensor.

Some embodiments of the present disclosure provide a wearable device including: (i) first sensing means, wherein the first sensing means are configured to detect a first hemodynamic property relating to a first portion of subsurface vasculature of a wearer of the wearable device; (ii) second sensing means configured to detect a second hemodynamic property relating to the wearer of the wearable device; (iii) mounting means configured to mount the first sensing means and the second sensing means to an external body surface of the wearer of the wearable device; and (iv) controller means operably coupled to the first and second sensing means, wherein the controller means are configured to perform operations including: (a) detecting, using the second sensing means, the second hemodynamic property relating to the wearer; and (b) detecting, using the first sensing means, the first hemodynamic property relating to the first portion of subsurface vasculature, wherein using the first sensing means to detect the first hemodynamic property of the first portion of subsurface vasculature includes operating the first sensing means based at least on the second hemodynamic property detected using the second sensing means.

Some embodiments of the present disclosure provide a method including: (i) mounting a wearable device to an external body surface of a wearer, wherein the wearable device includes: (a) a first sensor, wherein the first sensor is configured to detect a first hemodynamic property relating to a first portion of subsurface vasculature of the wearer; (b) a second sensor configured to detect a second hemodynamic property relating to the wearer; (c) a mount configured to mount the first sensor and the second sensor to the external body surface such that the first sensor is proximate to the first portion of subsurface vasculature; and (d) a controller operably coupled to the first and second sensors, wherein the controller comprises a computing device; (ii) operating, by the controller, the second sensor to detect the second hemodynamic property relating to the wearer; and (iii) operating, by the controller, the first sensor to detect the first hemodynamic property relating to the first portion of subsurface vasculature, wherein operating the first sensor to detect the first hemodynamic property of the first portion of subsurface vasculature comprises operating the first sensor based at least on the second hemodynamic property detected using the second sensor.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 6 is a block diagram of an example system that includes a plurality of wearable devices in communication with a server.

DETAILED DESCRIPTION

Figure 1:
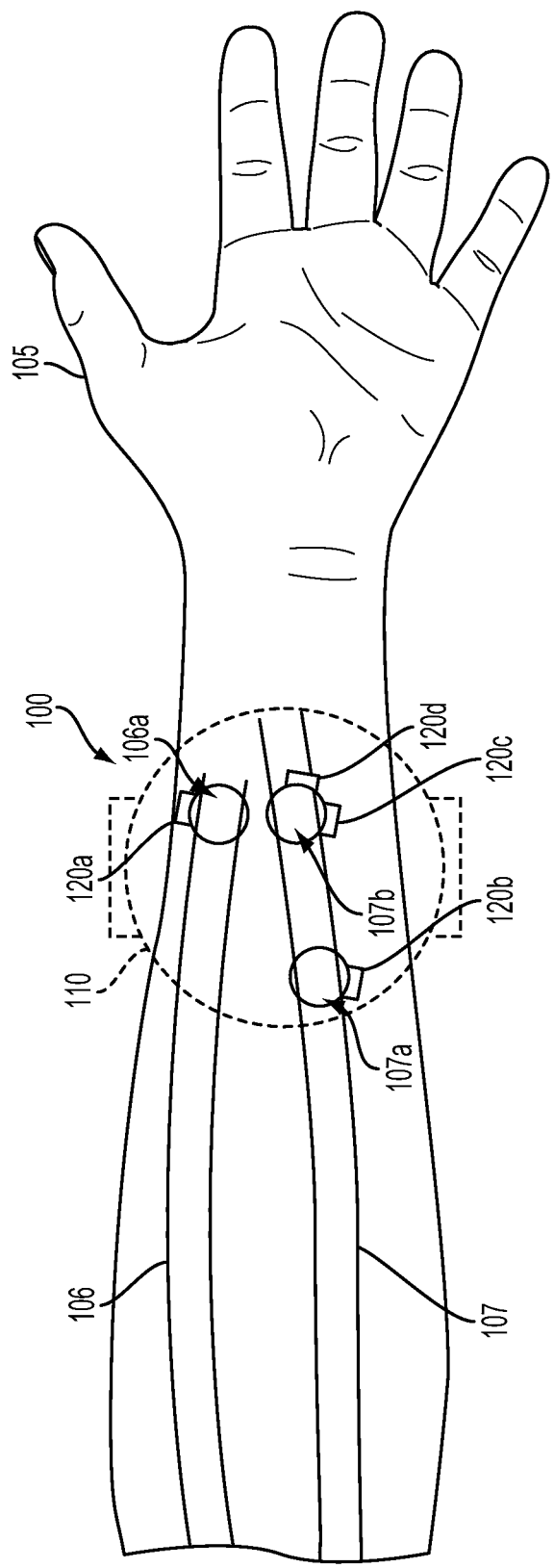
FIG. 1 is a view of an example wearable device while on a human arm.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where the operation of two or more sensors to locate the relative positioning of a target is desired. The environment may be any living or non-living body or a portion thereof, a gel, an emulsion, a fluid conduit, a fluid reservoir, etc. For example, one of skill in the art will recognize that the embodiments disclosed herein may be used to sense flow or other properties in or of some other environment of interest (e.g., a fluid conduit, pipe, or tube) within a manufactured device or industrial environment or work piece.

I. OVERVIEW

A wearable device may be configured to perform a variety of different functions and/or applications. In some examples, a wearable device is configured to measure physiological parameters (e.g., one or more hemodynamic properties) of the wearer. Measuring physiological properties of the wearer could include interacting with (e.g., receiving light from, detecting an electrical current or potential related to, illuminating, detecting some other property of) one or more portions of subsurface vasculature or other elements of the cardiovascular system within the body of the wearer. For example, detecting the timing, frequency, flow rate, or other information about blood flow within a portion of vasculature (e.g., a vein or artery) beneath the skin of the wearer could include illuminating and detecting light received from the portion of subsurface vasculature. Such information (e.g., hemodynamic properties) detected using two or more sensors could be used to determine a health state or other information of the wearer. Using information detected using two sensors could allow for the determination of such information with a higher accuracy, sensitivity, bandwidth, or according to some other improved condition. Additionally or alternatively, determination of information about the wearer could be allowed by the operation of a first sensor to detect a first hemodynamic or other property of the wearer (e.g., of a portion of subsurface vasculature of the wearer) based on information (e.g., hemodynamic properties) detected using a second sensor. For example, a timing of operation, a filter frequency response or frequency cutoff, an illumination amplitude, an amplifier gain, or some other operational parameter of the first sensor could be controlled based on a heartbeat timing, heartbeat phase, blood flow rate, blood oxygenation, blood volume in a portion of subsurface vasculature, or some other hemodynamic property or other physiological parameter of the wearer detected using the second sensor.

Detected hemodynamic properties of a wearer could include a variety of properties of a wearer's heart, a wearer's blood, one or more portions of subsurface or other vasculature of the wearer, blood within one or more portions of subsurface or other vasculature of the wearer, or some other information about the cardiovascular system of the wearer. Hemodynamic properties could include one or more of a flow rate, a pressure, a blood volume, a blood cell velocity and/or velocity profile, a blood oxygenation, a red blood cell content, a vessel diameter, or some other properties and/or features of one or more portions of vasculature of a wearer and/or blood therein at one or more points in time. Such properties could be detected at/in different portions of subsurface vasculature (e.g., two portions of vasculature in a wrist, upstream and downstream portions of an artery, vein, or other blood vessel) or in the same portion of subsurface vasculature (e.g., a flow rate and a volume of blood in a single portion of subsurface vasculature). For example, hemodynamic properties of the radial and ulnar artery of the wrist could be detected. In another example, a hemodynamic property of vasculature in a wrist and in vasculature of the head or torso (e.g., behind the ear) could be detected. Further, electrocardiograms or other hemodynamic properties of the wearer could be detected at one or more locations.

Sensors used to detect hemodynamic properties of a wearer (e.g., of portions of subsurface vasculature of a wearer) could include a single type of sensor or a plurality of sensor types. The plurality of sensors could include temperature sensors, energy sensors, electromagnetic sensors, light sensors, chemical sensors, acoustical sensors, infrared sensors, ultraviolet sensors, tonometers, electrocardiogram electrodes, tissue impedance electrodes, or other types of sensors. For example, the plurality of sensors could include photodetectors (e.g., light detectors, color detectors, polarity detectors, infrared detectors, ultraviolet detectors, cameras). In some examples, one or more of the plurality of sensors could include energy emitters (e.g., light emitters, heaters, acoustical transducers, current sources, voltage sources) configured to enable detection of some hemodynamic property of a body of a wearer (e.g., of a portion of subsurface vasculature of the wearer) by illuminating, heating, injecting a current into, applying a voltage to, or otherwise introducing an energy to the one or more portions of the body of the wearer. For example, the sensors could include one or more Doppler ultrasonography probes. In some examples, sensors could include active optical sensors configured to illuminate a portion of subsurface vasculature and/or blood therein and the detect light responsively emitted from the portion of subsurface vasculature. Such sensors could include laser Doppler flowmeters, dynamic laser speckle sensors, photoplethysmographic sensors, fluorescence imagers, or some other active and/or passive optical sensors.

Sensors could be configured to detect similar hemodynamic properties (e.g., first and second sensors configured to detect blood flow) or different hemodynamic properties (e.g., a first sensor configured to detect blood flow and a second sensor configured to detect blood volume in a portion of vasculature). Further, sensors could be configured to detect similar hemodynamic properties by similar means (e.g., first and second sensors configured to detect timing of blood pulses using photoplethysmographic means) or different means (e.g., a first sensor configured to photoplethysmographically detect heartbeat timing from blood volume in a portion of subsurface vasculature and a second sensor configured to detect heartbeat timing using electrodes to detect an electrocardiographic signal).

The operation of a first sensor to detect hemodynamic properties could be informed by hemodynamic properties detected using a second sensor. For example, a second sensor could be configured to detect a timing of heartbeats of a wearer (e.g., by detecting a timing of blood pulses in a portion of subsurface vasculature or by detecting an electrocardiographic signal from the wearer) and a first sensor could be operated to detect a velocity of blood flow or some other hemodynamic property of a portion of subsurface vasculature at particular points in time relative to heartbeats of the wearer (e.g., to improve a signal-to-noise ratio (SNR) of the property measured by the second sensor or to detect the blood flow or other hemodynamic property at a specified point in the cardiac cycle). One or more filter coefficients, light emitter amplitudes, or other properties of a first sensor (e.g., a dynamic laser speckle sensor) could be set based on a heartbeat timing and/or phase, blood flow, blood volume, or other hemodynamic property detected by a second sensor (e.g., a photoplethysmographic sensor) according to an application (e.g., to maximize an SNR of an output of the first sensor, to minimize saturation or other nonlinear effects in the first sensor, to reduce an overall power consumption of the first sensor).

A health state or other physiological property of a wearer could be determined based on a combination of hemodynamic properties detected using two or more sensors. This could include averaging two or more detected hemodynamic properties (e.g., averaging measured flow rates detected using two different sensors) or otherwise combining such information to determine an estimate of the hemodynamic property that has less noise or that is improved in some other way. In some examples, a health state could be determined by combining two or more similar or dissimilar detected hemodynamic properties using principal components analysis, independent components analysis, non-negative matrix factorization, or some other linear or nonlinear combination. In some examples, a model of one or more aspects or elements of the wearer could be used to determine a health state of the wearer based on two or more detected hemodynamic or other properties.

In some examples, determination of a health state or other physiological property of a wearer could be enabled by the detection of one or more hemodynamic properties (e.g., hemodynamic properties of subsurface vasculature) at two or more locations in the body of a wearer. For example, a degree of arterial stiffness of an artery could be determined by measuring a flow rate of blood at upstream and downstream locations of the artery, determining a pressure wave velocity in the artery based on the detected flow rates, and determining the arterial stiffness based on the pressure wave velocity in the artery. Further, a health state of a wearer could be determined based on hemodynamic properties of subsurface vasculature detected at different points in time.

In some examples, the wearable device may include a user interface that is configured to provide user-discernible indications (e.g., visual, audible, and/or tactile indications) of information sensed by sensors of the wearable device, progress or other information related to a function of the device, or other information. In some examples, the user interface could additionally provide a means for one or more settings of the wearable device (e.g., a sampling rate, a user information privacy setting, a user's credentials to access a service) to be specified by a wearer according to the wearer's preferences. In some examples, the wearable device may include a wireless communication interface that can transmit/receive data to/from an external device, for example, using Bluetooth, ZigBee, WiFi, and/or some other wireless communication protocol. The data transmitted by the wireless communication interface may include data indicative of one or more physiological parameters or health state measured and/or determined by the device, a blood oxygenation level, a blood flow rate, a blood pressure, or the concentration of an analyte in the blood of the wearer. The wireless communications interface could additionally or alternatively be configured to receive data from an external system.

II. EXAMPLE HEMODYNAMIC PROPERTIES AND DETECTION THEREOF

Hemodynamic properties can include any properties of the blood, vasculature, heart, or other elements of the cardiovascular system or related tissues of a person. Hemodynamic properties could be related to one or more chronic or acute health states of a person (e.g., hypertension, hypotension, hyperglycemia, hypoglycemia, panic attack, stroke, heart attack, blood loss) and measurement of one or more hemodynamic properties of the person could allow determination and/or monitoring of such health states. Hemodynamic properties include instantaneous properties (i.e., properties that be measured at a single point in time, e.g., a flow rate of blood in a particular portion of vasculature at a particular point in time) and/or properties of the body of a person that are related to changes in a body over time (e.g., a rate of heartbeats, a mean blood flow over one or more heartbeats, a mean cardiac output, a cardiac output waveform). Hemodynamic properties include properties that can be measured at a single location on or within a body (e.g., a blood pressure, flow rate, or other properties of blood in a particular portion of vasculature) and properties that can be measured at and/or between multiple locations on or within a body (e.g., a pulse wave velocity in an artery measured by detecting a blood flow rate, volume, or other property at two or more locations of the artery).

Hemodynamic properties could include a flow rate, a flow profile, a velocity, a velocity profile, a pressure, a level of oxygenation, a blood cell content, a volume, a density, a chemical content, a cell content, an analyte content, a viscosity, or some other property of blood at one or more locations (e.g., in one or more portions of subsurface or other vasculature) in the body of a person. Hemodynamic properties could also include a diameter, a stiffness, a pulse wave velocity, a fluid impedance, a degree of perfusion and/or leakiness, or some other property of one or more portions of subsurface or other vasculature. Hemodynamic properties could include a timing, rate, rate variability, blood flow waveform, blood pressure waveform, or other properties of heartbeats of a heart measured at one or more locations on or within a body. Hemodynamic properties could include a Q-T interval, a presence, absence, or other property of a P, QRS, T, or other wave, or some other property of an electrocardiogram measured between two points on or within a body. Further hemodynamic properties could include properties derived from two or more detected and/or determined hemodynamic properties or other physiological properties of a body. For example, hemodynamic properties could include a mean cardiac output, an instantaneous cardiac output, or some other property of the functioning of the heart determined, e.g., by multiplying a heart rate (e.g., a heart rate determined from a detected ECG waveform) by a total volume of blood pumped in a single cardiac cycle (e.g., a total volume of pumped blood determined based on a detected blood flow rate in a portion of subsurface vasculature).

Hemodynamic properties could be detected and/or determined using a variety of sensors disposed at a variety of location on, within, or otherwise proximate to a human body. Sensors could be emplaced within a body (e.g., surgically implanted, inserted via catheter and/or needle), mounted to the outside of the body (e.g., adhered, strapped, mounted, or otherwise disposed proximate to an external body surface), or configured to detect one or more hemodynamic properties of a body from a distance. Sensors could include electrodes or other elements configured to provide electrical, thermal, mechanical, chemical, fluidic, or other access to tissues of a body. Sensors could be configured to emit and/or receive light (e.g., ultraviolet radiation, infrared radiation, visible light), acoustical waves, electric fields, magnetic fields, or other energy toward/from portions of vasculature (e.g., portions of subsurface vasculature) or other tissues of a body.

Sensors configured to detect hemodynamic properties of a human body could be included as part of a device configured to mount the sensor on or near the human body, e.g., on an external body surface of the human body. For example, FIG. 1 illustrates an arm 105 including a radial artery 106 and an ulnar artery 107. A wearable device 100 includes a mount 110 configured to mount sensors 120a, 120b, 120c, 120d proximate to an external body surface of the arm 105 (e.g., a wrist surface of the arm 105). A first sensor 120a is positioned by the mount 110 proximate a first portion of subsurface vasculature 106a such that the first sensor 120a can detect a hemodynamic property of the first portion of subsurface vasculature 106a. A second sensor 120b is positioned by the mount 110 proximate a second portion of subsurface vasculature 107a such that the second sensor 120b can detect a hemodynamic property of the second portion of subsurface vasculature 107a. Third 120c and fourth 120d sensors are positioned by the mount 110 proximate a third portion of subsurface vasculature 107b such that the third 120c and fourth 120d sensors can detect a hemodynamic property of the third portion of sub surface vasculature 107b.

Note that the location of the sensors 120a-d proximate portions of subsurface vasculature 106a, 107a, 107b by a single mount 110 is intended as an illustrative example of the systems and methods described herein. A greater or fewer number of sensors could be included and could be disposed proximate to a greater or fewer number of portions of subsurface vasculature, deep vasculature, or other tissues of a body. Further, systems and methods described herein could be embodied including multiple housings, mounts or other elements configured to mount sensors or other components proximate external body surfaces or other locations or tissues of a body of a person. Such multiple mounts, housings, or other elements could be connected via wires, cables, tethers, hinges, or other elements according to an application and/or could be in wireless communication to enable some applications. Additionally or alternatively, sensors could be disposed as part of handheld, desktop, or other device(s) configured to be brought into contact with an external body surface or other tissue and/or to detect properties (e.g., hemodynamic properties) of a body from a distance. Further sensors could be configured to detect further properties of a body and/or the environment of a body in addition to or in alternative to hemodynamic properties of the body.

The disposition of sensors at a variety of locations could allow for the determination of a variety of hemodynamic or other properties of a body. In some examples, hemodynamic or other properties of the body could be detected in multiple portions of subsurface vasculature or other tissues of a body to allow for determination of a hemodynamic property or health state of the body (e.g., of tissues disposed between, upstream relative to a blood flow, or otherwise proximate to the multiple portions of subsurface vasculature or other tissues). For example, hemodynamic properties could be detected in multiple portions of subsurface vasculature that are part of the same blood vessel (e.g., artery or vein). This could allow the detection and/or determination of a pulse wave velocity, an arterial stiffness, a blood perfusion rate from a segment of the blood vessel disposed between the multiple portions of subsurface vasculature, a blood pressure, blood pressure differential, and/or blood pressure gradient within/proximate to the blood vessel, or some other hemodynamic or other property of a body. For example, hemodynamic or other properties of the second 107a and third 107b portions of subsurface vasculature could be detected (e.g., using the second 120b and third 120c and/or fourth 120d sensors) and used to determine one or more properties of the ulnar artery 107.

In some examples, multiple hemodynamic or other properties of the body could be detected in a single portion of subsurface vasculature. This could allow the determination of some further hemodynamic or other property of the portion of subsurface vasculature, e.g., the determination of a blood pressure, a blood pressure waveform, a blood flow rate, a stiffness of the portion of subsurface vasculature, or some other properties of the portion of subsurface vasculature. This determination could include using multiple detected hemodynamic properties to determine a further hemodynamic property or health state using a model, an algorithm, and decomposition, or some other computational method. In some examples, such computational methods could include using a hemodynamic property detected using a first sensor (e.g., a blood flow rate sensor with a low resolution and/or low accuracy) to adjust, calibrate, or otherwise interpret an output of a second sensor (e.g., a blood flow rate sensor with a higher resolution).

Additionally or alternatively, the operation of a first sensor to detect a hemodynamic property of a portion of subsurface could be based on a hemodynamic property of the portion of subsurface vasculature (or of some other element or portion of a body) detected using a second sensor. For example, the third sensor 120c could be a dynamic laser speckle sensor configured to measure blood flow rate and/or blood cell velocity in the third portion of subsurface vasculature 107b. The third sensor 120c could include a filter having a controllable cutoff frequency that could be set to increase a resolution, signal-to-noise ratio (SNR), an accuracy, or to otherwise improve an output of the third sensor 120c based on an estimate of the blood flow rate in the third portion of subsurface vasculature 107b. Such an estimate of the blood flow rate in the third portion of subsurface vasculature 107b could be provided by the fourth sensor 120d. For example, the fourth sensor 120d could be a photoplethysmographic sensor configured to generate an output related to a volume of blood in the third portion of subsurface vasculature 107b. The third sensor 120c could be operated based on an estimate of blood flow rate in the third portion of subsurface vasculature 107b that is determined based on a volume of blood in the third portion of subsurface vasculature 107b detected using the fourth sensor 120d.

Sensors (e.g., 120a-d) included in embodiments of systems or methods described herein could be similar or different sensors. For example, the sensors 120a-d of the wearable device 100 could all be the same type of sensor (e.g., photoplethysmographic sensors configured to optically detect a volume of blood in respective portions of subsurface vasculature or other portions of tissue) or different sensors. Further, such sensors (e.g., 120a-d) could detect similar or different hemodynamic properties by similar or different means. In an example, the third 120c and fourth 120d sensors could be a dynamic laser speckle sensor and a Doppler ultrasonography probe, respectively, configured to measure a blood flow rate in the third portion of subsurface vasculature 107b. In another example, the third 120c and fourth 120d sensors could be a dynamic laser speckle sensor and a tonometer, respectively, configured to measure a blood flow rate and a blood volume, respectively, in the third portion of subsurface vasculature 107b. A timing of heartbeats and/or of pulses of blood flow or some other hemodynamic property in the third portion of subsurface vasculature 107b could be determined based on the output of one or both of the third 120c or fourth 120d sensors.

Sensors (e.g., 120a-d) included in embodiments of systems or methods described herein could include a variety of types of sensors configured in a variety of ways to detect a variety of different hemodynamic properties according to an application. Sensors could be configured to be in electrical, thermal, mechanical, fluidic, chemical, or some other form of contact or access with tissues of a body. This could include a sensor having one or more electrodes or probes having a specified electrical, thermal, or other resistance and configured to allow a flow of heat energy, electrical current, or some other energy through the electrodes or probes. For example, a sensor could include one or more thermal probes configured to allow a temperature of tissue in contact with the thermal probe(s) to be detected and/or for heat energy to be provided and/or removed from tissue in contact with the thermal probe(s). In some examples, a sensor could include two or more electrodes configured to allow a voltage between two or more respective portions of tissue in contact with the electrodes to be measured, to allow a current through the two or more electrodes to be measured, to allow a current and/or voltage to be provided to the portions of tissue, or to allow some other electrical interaction with tissue. For example, two or more electrodes could be configured to provide one or more electrocardiographic, tissue impedance, Galvanic skin potential, Galvanic skin resistance, or other electrical properties of a body to be detected.

A sensor could include one or more mechanical probes configured to detect a force and/or displacement of tissue in contact with the mechanical probe(s) and/or to transduce acoustical (e.g., ultrasonic) vibrations or energy into tissue. For example, a sensor could include a tonometer configured to detect a blood pressure, a blood volume, or some other property of subsurface vasculature beneath a portion of skin with which a mechanical probe or other element of the tonometer is in contact. In another example, a sensor could include one or more ultrasonic transducers configured to emit ultrasonic pulses or other acoustical energies into tissue and/or to receive ultrasonic pulses or other acoustical energies from tissue in contact with the one or more ultrasonic transducers. For example, a sensor could include a Doppler ultrasonography probe configured to transmit pulses and/or continuous waves of ultrasound energy into tissue (e.g., into a portion of subsurface vasculature, via intervening skin or other tissue) and to receive pulses and/or continuous waves of ultrasound energy from the tissue. One or more properties (e.g., a frequency shift relative to a frequency of ultrasound energy emitted by the sensor, a time delay and/or amplitude of a received pulse relative to an emitted pulse) of the received ultrasound energy could be used to determine a velocity of blood or other fluids in the tissue, to detect the location of tissues and/or boundaries between tissues, or to detect some other hemodynamic or other property of a body that includes the tissue.

Sensors could be configured to emit energy toward/into portions of tissue (e.g., portions of subsurface vasculature) and/or to receive energy emitted from portions of tissue to allow detection of hemodynamic or other properties of a body. Sensors could be configured to emit and/or receive light (e.g., visible, infrared, or ultraviolet light), electromagnetic radiation, acoustical vibrations (e.g., pulses of ultrasound), electrical fields, magnetic fields, or some other directed energy or energy field(s). In some examples, energy (e.g., light at an excitation wavelength of a fluorophore in tissue or blood, light at an absorption wavelength of red blood cells) could be emitted into a tissue, and energy responsively emitted from the tissue (e.g., light at an emission wavelength of an excited fluorophore, light reflected, scattered, refracted, or otherwise interacted with by blood or other tissue) could be detected and used to determine hemodynamic or other properties of a body. In such examples, one or more properties or features of an excitation spectrum, an abruption spectrum, an emission spectrum, a scattering spectrum, or some other optical property of tissues (e.g., of blood within a portion of subsurface vasculature) could be detected at one or more points in time to allow detection of hemodynamic or other properties of a body.

Optical sensors configured to emit light into/toward and/or to receive light emitted from a portion of subsurface vasculature could be configured in a variety of ways to detect a variety of properties of received light and/or to emit light having one or more specified and/or controlled properties. Such sensors could be configured to emit light in a beam having a round, linear, or other cross-sectional shape or to emit light to illuminate a broad region of a body. The direction of a beam of illumination emitted by a sensor could be fixed or controllable (e.g., by the operation of galvanometers or other actuators to control mirrors, lenses, or other optics of the sensor and/or to control a location or orientation of a sensor). Emitted light could be coherent, non-coherent, and/or could have a specified coherence length. Emitted light could be substantially monochromatic (e.g., emitted by a laser) or could otherwise have a specified wavelength and/or spectral profile. Further, properties of emitted light (e.g., wavelength, amplitude, polarization, coherence length, direction, beam width or shape) could be changed over time (e.g., a tunable laser of a sensor could be operated to emit light at a first specified wavelength at a first point in time and to emit light at a second specified wavelength at a second point in time). Further, optical sensors could be configured to detect an amplitude, wavelength, direction of polarization, degree of polarization, spectral content, relative phase, or other properties at one or more points in time and further to detect such properties in light emitted from multiple portions of a body (e.g., from multiple directions relative to the sensor, e.g., the sensor could include a camera).

In some examples, such an optical sensor could be configured as a dynamic laser speckle sensor. That is, the optical sensor could be configured to detect time-varying patterns of constructive and destructive interference (e.g., speckle events, spatial contrast) in light emitted from portions of a body in response to illumination of the body by a beam of substantially coherent, monochromatic light emitted from the optical sensor. Detected time-varying patterns of constructive and destructive interference could be related to changing properties of tissues of the body (e.g., of blood within portions of subsurface vasculature of the body). A relationship between the time-varying patterns in the emitted light and the changing properties of a portion of tissue could be related to a depth of the tissue, a distance between the tissue and an external body surface via which the light is emitted, a coherence length and/or wavelength of illumination applied to the biological tissue, or some other properties of the body, the illumination applied to the tissues, and/or element(s) of the optical sensor used to receive light responsively emitted from the body.

The optical sensor could be configured and/or operated to detect any property or properties of emitted light from the body having a time dependence or other property that can be used to determine hemodynamic properties (e.g., a flow rate, a distribution of velocities of blood cells, or some other flow properties of blood or other fluids of the body) of subsurface vasculature or other portions of the body. Such properties could include an intensity, wavelength, spectrum, degree of polarization, direction of polarization, or some other property of received light emitted from one or more portions of a body. In some examples, this could include the optical sensor being configured to detect the intensity and/or some other property of the emitted light at a plurality of points in time. For example, the intensity could be detected at a sufficiently high rate to detect the presence or other properties of individual speckle events or other short-duration features of the detected intensity. Further, such detected time-varying patterns received from a plurality of different portions of tissue of a body and/or detected properties thereof (e.g., detected using a corresponding plurality of light-sensitive elements of an imager or camera of the optical sensor) could be combined to determine hemodynamic properties of the body (e.g., by determining a spatial contrast in images of the body detected using the optical sensor).

Additionally or alternatively, information about time-varying patterns of constructive and destructive interference in the received light could be detected by filtering, integrating, or otherwise performing some analog and/or digital operations on the received light. For example, an average intensity of the received light during a specified period of time (e.g., during an exposure having a specified duration) could be detected and used to determine hemodynamic properties (e.g., a blood flow rate) in a portion of subsurface vasculature. In some examples, a filter cutoff frequency, a filter passband, a filter or amplifier gain and/or attenuation level, an integration time, an exposure time, or some other property of the operation and/or configuration of the optical sensor to detect hemodynamic properties of a body could be controllable, i.e., the controllable aspect of the optical sensor could comprise an operational parameter of the optical sensor.

The use of multiple sensors to detect multiple hemodynamic or other properties of subsurface vasculature or other elements or portions of a body could allow a variety of applications. Multiple sensors could allow for the detection of multiple hemodynamic or other properties of a body and/or of one or more particular tissues (e.g., portions of subsurface vasculature) of a body. Multiple sensors could allow a particular hemodynamic property to be detected to a higher accuracy, to a higher precision, with a higher SNR, at a higher resolution, with a higher repeatability, with a lower thermal or other drift, or according to some other improved condition by combining the outputs of the multiple sensors (e.g., through averaging, a linear combination, or some other method). This could be due to averaging or other methods of combination of multiple sensor outputs allowing uncorrelated elements of the multiple sensor outputs (e.g., noise elements of the signals) to be rejected while keeping correlated elements (e.g., signals relating to a hemodynamic property of interest).

For example, the third 120c and fourth 120d sensors could be configured to detect a blood flow rate (or some other hemodynamic property) in the third portion of vasculature 107b, and the outputs of the third 120c and fourth 120d sensors could be averaged or otherwise combined to generate an estimate of the blood flow rate in the third portion of vasculature 107b that has a lower variability over time, a lower noise level and/or SNR, a higher accuracy, or that is otherwise improved relative to a measurement of blood flow in the third portion of vasculature 107b generated by either of the third 120c and fourth 120d sensors alone. In another example, the first 120a and third 120c sensors could be configured to detect a timing of heartbeats, a timing of pulses of blood, a blood pressure and/or a blood pressure waveform in blood, or some other hemodynamic property in first 106a and third 107b portions of subsurface vasculature, respectively. The outputs of the first 120a and third 120c sensors could be averaged or otherwise combined to generate an estimate of the detected hemodynamic property in the arm 105 that has a lower variability over time, a lower noise level and/or SNR, a higher accuracy, or that is otherwise improved relative to a measurement of the detected hemodynamic property generated by either of the third 120c and fourth 120d sensors alone. Additionally or alternatively, outputs of multiple sensors could be combined in a linear combination, according to a linear or nonlinear decomposition or dimensionality reduction (e.g., principal components analysis, non-negative matrix factorization), or by some other method according to an application.

Multiple sensors could allow for the detection and/or determination of a hemodynamic or other property of a body based on detected properties of the body by applying the detected properties to a model, algorithm, or other computational process. Such methods could be applied to hemodynamic or other properties of a body detected by multiple similar or different sensors (e.g., by two photoplethysmographic sensors, by a tonometer and a Doppler ultrasonography probe) detecting properties of one or more portions of the body (e.g., by two sensors detecting properties of the same portion of subsurface vasculature, by two sensors detecting properties of respective different portions of subsurface vasculature). In an example, a blood pressure in a particular portion of subsurface vasculature could be determined based on a detected flow rate and a detected change in volume of blood in the particular portion of vasculature. In another example, a pulse wave velocity in an artery (e.g., the ulnar artery 107) could be determined by detecting a timing of pulses of blood flow (e.g., by detecting a blood flow rate, a volume of blood, a blood oxygenation, or some other property of portions of the artery) at two or more points in the artery (e.g., the second 107a and third 107b portions of subsurface vasculature) using two or more sensors (e.g., 120b and 120c and/or 120d). Such determinations could be based on models of one or more elements of the body.

Such models could be based on an understanding of the physical principles operating in the body (e.g., a model based on an understanding of the dynamics of blood flow and pressure in an artery) and/or based on fitting of a generic model structure to a plurality of observations of a system (e.g., using 'black box' methods to set one or more parameters of a generic model structure such that outputs of the fitted model substantially match the outputs of a real system being modelled, given some set of inputs corresponding to properties of a body that are detectable by sensors). In some examples, such models could include linear or nonlinear dimensionality reduction and/or rotation methods (e.g., principal components analysis, independent components analysis, non-negative matrix factorization, In some examples, the output from a first sensor (or more than one sensor) could be used to remove an offset, a noise signal, an unwanted non-noise signal, or some other component from an output of a second sensor. For example, first and second sensors could measure the volume of blood in a particular portion of subsurface vasculature. The first sensor is configured to measure all frequency components of the blood volume, which include a high-frequency component relating to the pulsatile flow of blood due to individual heartbeats and a low-frequency component relating to slower changes in blood flow due to respiration. The second sensor is configured to measure only the high-frequency. An output of the second sensor could be subtracted from or otherwise used to remove the high-frequency component from the output of the first sensor, allowing the information about respiration to be determined. Other configurations and/or operations of two or more sensors to remove noise and/or unwanted signals from the outputs of one or more sensors are anticipated.

Further, hemodynamic properties detected by different sensors at different points in time could be combined and/or used in some other way as described herein (e.g., to produce combined measurements of hemodynamic properties) due to an effective delay, latency, or other time difference between properties detected by multiple sensors. For example, a blood flow rate in the second portion of subsurface vasculature 107a could be detected using the second sensor 120b at a first point in time and combined with a blood flow rate in the third portion of subsurface vasculature 107b could be detected using the third sensor 120c at a second point in time to produce an improved (e.g., having a higher accuracy, having a lower SNR) estimate of the blood flow rate in the ulnar artery 107. The second point in time could be later than the first point in time by a specified and/or determined delay between blood flow rates and/or blood flow rate waveforms measured at the second 107a and third 107b portions of subsurface vasculature, e.g., a delay related to a length of the ulnar artery 107 between the second 107a and third 107b portions of subsurface vasculature divided by a pulse wave velocity in the ulnar artery 107.

Multiple sensors could allow a first sensor to be operated based on hemodynamic or other properties detected using a second sensor (or more than one sensor) to improve operation of the first according to some application. In some examples, such a configuration could allow operation of the first sensor at a lower overall power by operating the sensor during specified periods of time relative to a measurement performed by the second sensor. For example, an overall sensor energy consumption could be reduced by operating the first sensor when an event of interest occurs (e.g., a peak blood volume in a portion of subsurface vasculature proximate the first sensor, an occurrence of tachycardia, hypertension, or some other health state) and disabling the first sensor otherwise, where the timing of the event of interest (e.g., a point in time and/or a period of time at/during which the event of interest occurs) is detected using the second sensor. In some examples, a first sensor could be operated based on hemodynamic properties detected by a second sensor to improve a sensitivity or other property of the first sensor by setting an operational parameter of the first sensor based on a measurement performed by the second sensor, or according to some other method.

The hemodynamic or other property detected by the second sensor could be similar to or different from the property detected by the first sensor. For example, the first and second sensors could be configured to detect the same hemodynamic property (e.g., a flow rate of blood in a particular portion of subsurface vasculature) and the second sensor could have a lower resolution or other property relative to the first sensor. The first sensor could be operated to produce a 'coarse' measurement of the hemodynamic property, which could be used to operate the first sensor (e.g., to set a gain, to set an offset, to set a sensitivity) such that the first sensor can operate to generate a higher-resolution 'fine' measurement of the hemodynamic property. In another example, the first sensor being operated based on a hemodynamic property detected by the second sensor could allow detection of the hemodynamic property by the first sensors more quickly (e.g., by starting an iterative measurement process at an initial estimate of the hemodynamic property to be measured that is based on an output of the second sensor).

Such operational parameters of a first sensor could include a gain (e.g., of an amplifier), a sampling rate, an integration interval, an exposure time, an attenuation factor, a filter coefficient or cutoff frequency of a filter, a selection of one or more filters from a set of filters in a switched filter bank, an operational mode (e.g., a selection between a pulsed mode for interrogation/illumination of a portion of subsurface vasculature and a continuous mode for interrogation of the portion of subsurface vasculature), or some other property of the configuration and/or operation of the first sensor. In some examples, such operational parameters could include parameters describing illumination or other energy used to illuminate, excite, or otherwise interact with a target tissue or other elements of a body. For example, operational parameters could include an amplitude, a wavelength, a spectral content, a coherence length, a pulse rate, a pulse duty cycle, a pulse frequency, a waveform, a degree of polarization, a direction of polarization, a beam width, a beam shape, a beam direction, a beam dispersion, or some other property of light emitted from a first sensor.

Figure 2A:
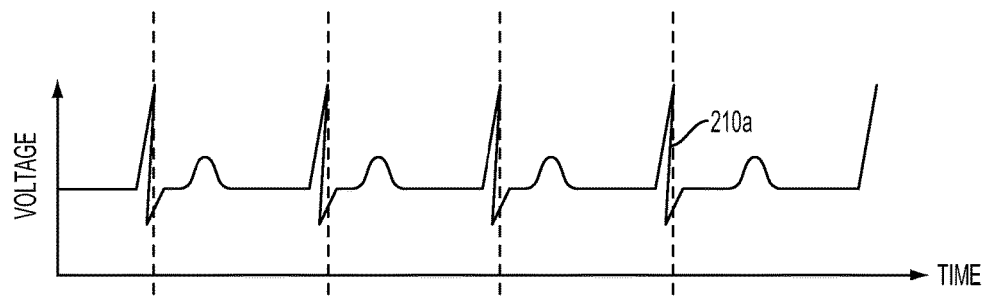
FIG. 2A is an example output of a sensor configured to detect a hemodynamic property of a human.
Figure 2B:
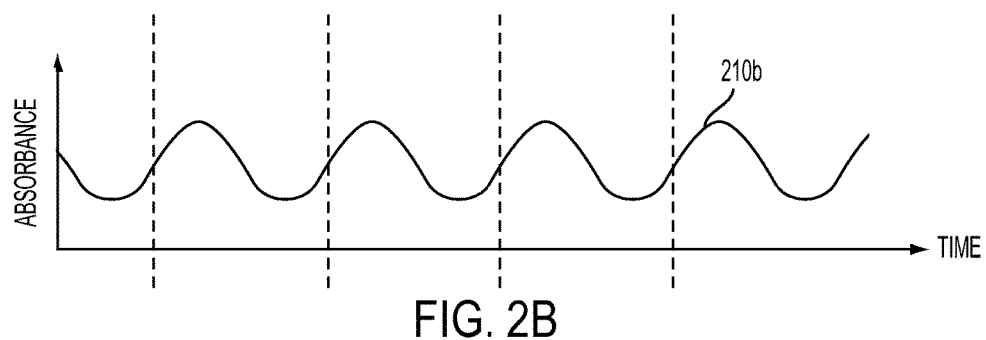
FIG. 2B is an example output of a sensor configured to detect a hemodynamic property of a human.

To illustrate such operations of first sensors based on properties measured by second sensors, FIGS. 2A and 2B are example detected hemodynamic properties (an ECG voltage waveform 210a detected from the voltage between two electrodes in contact with respective portions of a body and a blood volume waveform 210b detected from the absorbance of an emitted light by a portion of subsurface vasculature of the body, respectively) detected by sensors that could be included and/or operated as part of a system or method as described herein. Note that the determined and/or detected signals of FIGS. 2A-2F are plotted on the same timescale; that is, the vertical dashed lines coinciding with QRS waves in the ECG waveform 210a correspond in time to the vertical dashed lines of the other waveforms of FIGS.

2B-2F. Further, the correspondence of the vertical dashed lines to QRS complexes in the ECG waveform 210a implies that the times indicated by the vertical dashed lines fall at relatively the same point in each cycle of the heartbeat (e.g., at a similar phase within the repeating cycle of the heartbeats of the body).

Figure 2C:
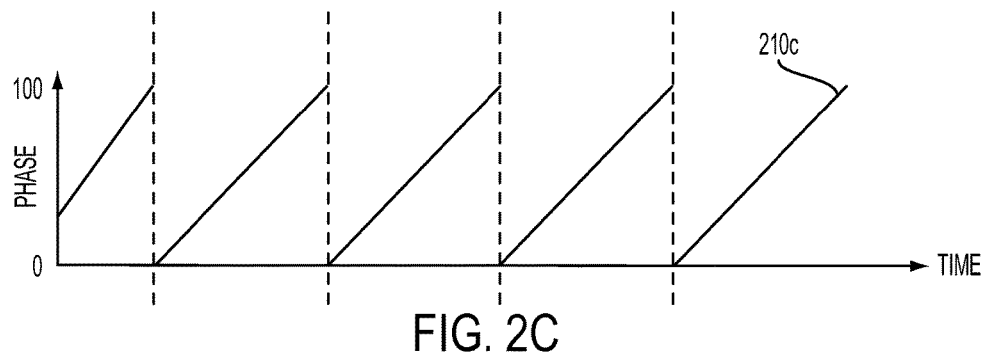
FIG. 2C is an example timing diagram generated based on an output of a sensor configured to detect a hemodynamic property of a human.

In some examples, a sensor could be operated relative to the timing of heart beats or some other repeating process of a body. This could include, based on one or more instances of the repeating process (e.g., based on a detected timing of one or more heartbeats), determining a phase of the repeating process. As an example, FIG. 2C shows a pulse phase waveform 210c determined based, for example, on the detected ECG waveform 210a such that 0% of the phase waveform corresponds to the timing of individual QRS waves in the ECG waveform 210a. 0% for such a phase waveform could be defined and/or determined based on other features of an ECG waveform (e.g., based on a maximum of a T-wave in an ECG waveform, based on one or more particular features within a QRS wave in an ECG waveform) or could be based on features of some other detected, repeating waveform (e.g., based on the timing of maxima in the detected blood volume waveform 210b).

A timing of operation of a sensor could be based on such a determined phase, e.g., a sensor could be operated to detect a hemodynamic property at one or more specified points or periods during the phase of a detected repeating process. For example, a sensor could be operated at points in time when the determined pulse phase waveform 210c is substantially equal to 35% or some other specified point(s) or period(s) during the pulse phase 210c. Additionally or alternatively, one or more operational parameters of a sensor could be controlled based on such a determined phase (e.g., a gain or other parameter of a sensor could be controlled according to a function of the phase, a first filter in a filter bank could be used during a first period during the determined phase and a second filter in the filter bank could be used during a second period).

A phase of some detected repeating process (e.g., a detected QRS wave in the ECG waveform 210a, a detected volume maximum in the blood volume waveform 210b) could be determined by a variety of methods. In some examples, an expected repeated process duration or frequency (e.g., an expected heart rate) could be specified or determined and used to determine the phase based on one or more recently detected instances of a feature (e.g., a QRS wave) of the repeated process. For example, a phase could be determined by determining an elapsed time since the most recent detected QRS wave in the ECG waveform 210a and dividing this elapsed time by an expected heartbeat duration. Such an expected heartbeat duration could be specified (e.g., set to 1 second) or could be determined based on one or more previously detected QRS waves or other features of the ECG waveform 210a (e.g., determined from the time difference between the two most recently detected QRS waves, determined from an average heart rate during a previous time period from a plurality of detected QRS waves or other detected features of the ECG waveform 210a). In some examples, multiple features of a detected repeated process could be used to determine a phase (e.g., the pulse phase waveform 210c could be based on the timing of one or more previous QRS waves and the timing of one or more previous T waves).

Figure 2D:
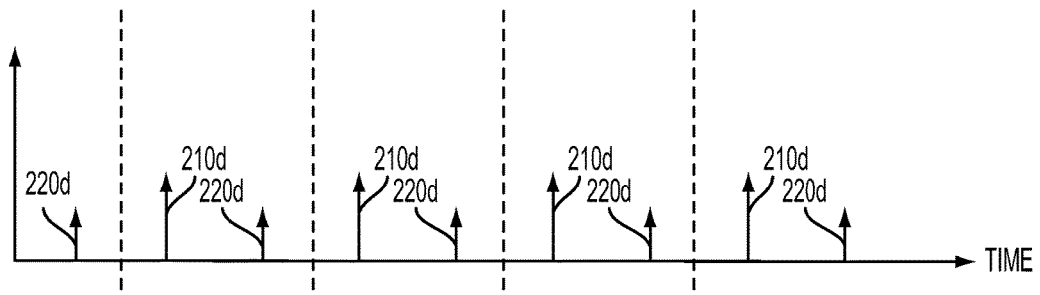
FIG. 2D is an example timing diagram generated based on an output of a sensor configured to detect a hemodynamic property of a human.

In some examples, a sensor could be operated relative to the timing of some other detected event of a body. This could include detecting a timing of a maximum, a minimum, a peak, an inflection point, a maximum rate of change, a minimum rate of change, the reaching of a threshold, a waveform matching some specified pattern, or some other feature or aspect of a detected property of a body. As an example, FIG. 2D shows the timing of blood volume maxima 210d and blood volume minima 220d determined from the detected blood volume waveform 210b. Other determined timings could be defined and/or determined based on other features of a detected blood volume or based on some other detected property of a body. In some examples, operation of a first sensor could be based on a detected timing of QRS waves in the ECG waveform 210a, based on the detected blood volume 210b remaining at a specified level or within a specified range for a specified period of time, based on a detected blood flow rate reaching a maximum, based on a detected blood flow rate exceeding a specified threshold, or based on some other feature, element, or behavior of a hemodynamic or other property of body detected using a second sensor.

Figure 2E:
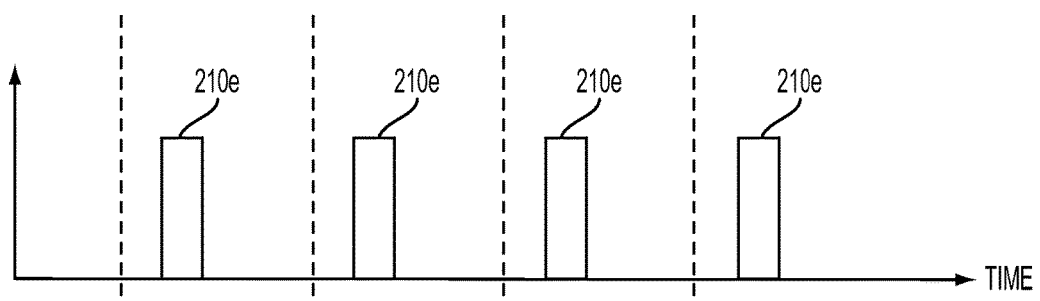
FIG. 2E is an example timing diagram of operation of a sensor configured to detect a hemodynamic property of a human.

The timing of operation of a first sensor could be based on a detected and/or determined timing, phase, or other information related to a property of a body detected using a second sensor. As an example, FIG. 2E shows the timing of periods of operation 210e of a sensor based on determined timings of blood volume maxima 210d. In this example, the detection of a maximum in the blood volume waveform 210b (indicated in FIG. 2D by 210d) causes a sensor to operate to detect some hemodynamic property (e.g., a flow rate of blood in the portion of subsurface vasculature whose blood volume is represented by 210b) during a specified subsequent period of time (indicated by 210e). In some examples, this could include operating the sensor to perform a single measurement; alternatively, the sensor could be operated to perform a plurality of measurements. In some examples, the subsequent periods of time could have a specified duration; additionally or alternatively, the sensor could be operated during periods of time whose durations are specified or determined by some other method (e.g., to operate until a detected hemodynamic property has reached a maximum or exhibited some other behavior, to operate from a first determined timing (e.g., a blood volume maximum of 210d) until a subsequent determined timing (e.g., a blood volume minimum of 220d), until a detected and/or determined health state has changed).

The timing of operation of a sensor (e.g., 210e) could be controlled based on a determined timing of some other detected property (e.g., as shown in the examples of FIGS. 2B, 2D, and 2E), based on a detected or determined phase (e.g., at one or more specified points during the determined phase, during a range of phases of the determined phase) of a repeated process of a detected hemodynamic property, or according to some other detected or determined timing information. Additionally or alternatively, one or more operational parameters (e.g., one or more controlled properties of a filter frequency response, a selection of a filter from a switched filter bank, an amplifier gain setting, a sampling rate, an intensity, direction, wavelength, pulse timing, pulse waveform, or other properties of an emitted light) of the sensor could be controlled based on such timing information (e.g., detected timing of events, a detected or determined phase of a repeated process) and/or some other detected property of a body (e.g., a hemodynamic property of a portion of subsurface vasculature).

Figure 2F:
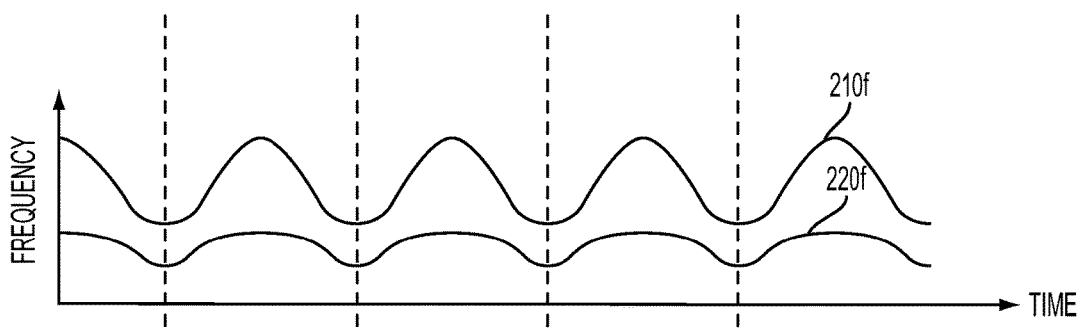
FIG. 2F is an example timing diagram of operation of a sensor configured to detect a hemodynamic property of a human.

As an example, FIG. 2F shows a controlled lowpass filter cutoff frequency 210f and a controlled lowpass filter cutoff frequency 220f of a bandpass filter of a sensor (e.g., cutoff frequencies of a filter and/or amplifier of a dynamic laser speckle sensor, a Doppler ultrasonography sensor, or some other type of sensor). The values of the controlled cutoff frequencies 210f, 220f are based on the determined pulse phase waveform 210c. In this example, the controlled cutoff frequencies 210f, 220f are determined for a particular point in time based on a lookup table, formula, algorithm, or other method that generates lowpass 210f and highpass 220f cutoff frequencies based on the determined pulse phase 210c for the particular point in time.

Additionally or alternatively, operational parameters of a first sensor (e.g., controlled filter cutoff frequencies 210f, 220f) could be controlled based on a value of one or more hemodynamic properties, health states, or other properties of a body detected using a second sensor. For example, the values of the controlled cutoff frequencies 210f, 220f could be based on the detected blood volume waveform 210b (e.g., determined by applying a detected value of the blood volume to a formula, model, lookup table, or some other algorithm to generate the controlled cutoff frequencies 210f, 220f). This could be done due to a dependence of the operation of the first sensor (e.g., a dependence of a sensitivity, an SNR, a noise characteristic and/or statistic of the first sensor and/or of an output of the first sensor) on one or more corresponding properties of a body and/or tissue thereof measured by the first sensor.

For example, a dynamic laser speckle sensor (or some other sensor, e.g., a laser Doppler flowmeter) could be configured to detect a flow rate of blood in a manner depending on the value of one or more operational parameters of the sensor (e.g., a cutoff frequency, bandwidth, center frequency, or other filter property of a filter of the dynamic laser speckle sensor or laser Doppler flowmeter) relative to the value of the flow rate of blood to be measured. That is, an SNR, a noise characteristic, an accuracy, or some other property of the output of the dynamic laser speckle sensor could be optimized, relative to the value of the flow rate of blood to be measured, by controlling one or more operational parameters (e.g., cutoff frequencies of a filter of the dynamic laser speckle sensor) to have some specified value based on the flow rate of blood to be measured. The flow rate of blood to be measured could be measured directly (e.g., by the dynamic laser speckle sensor using some previous estimate of the flow rate of blood, by some other sensor), or could be estimated through some other method. In some examples, a related property could be detected (e.g., the blood volume waveform 210b) and used to estimate the flow rate of blood (e.g., using a linear or nonlinear function or some other method to estimate the flow rate of blood based on the blood volume). Additionally or alternatively, the flow rate of blood could be estimated based on a detected or determined pulse phase of the body (or a detected or determined phase of some other repeated process of a body). Other sensors, controlled operational parameters thereof, properties of a body related to operation of such sensors, and systems and methods for detecting and/or estimating such properties of a body are anticipated.

Operation of a first sensor (e.g., control of one or more operational parameters of the first sensor) could be based on other information detected and/or determined using a second sensor, previous operation of the first sensor, some further sensor(s), or according to some other application. For example, the first sensor could be operated based on a health state and/or a change of a health state detected by the first sensor, the second sensor, or generated by some other method. A sample rate, a resolution, a power use, or some other operational parameter of a sensor could be controlled based on the detection or determination that a body is experiencing a particular health state. For example, the detection that a body was experiencing hypoglycemia, hypotension, hypertension, atrial or ventricular fibrillation or arrest, heart palpitations, a stroke, a heart attack, a panic attack, a seizure, or some other health state of interest could result in operation of the first sensor to detect one or more properties of the body (e.g., hemodynamic properties of a portion of subsurface vasculature) and/or to detect such properties at an increased rate or according to some other application. Detection of such a health state could include operating the first sensor or some other sensor(s), an input provided via a user interface of a device, or by some other method.

Figure 3A:
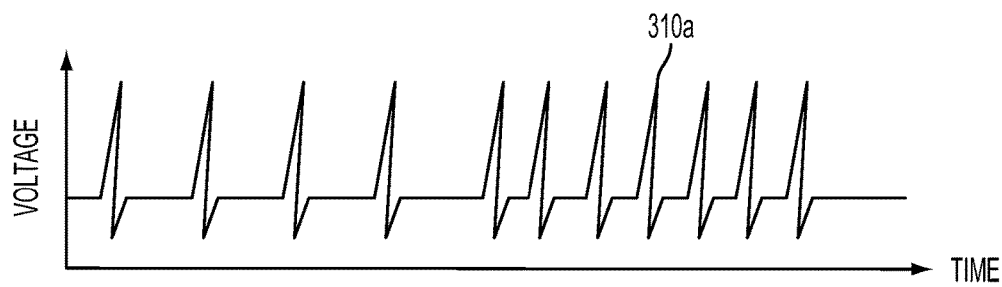
FIG. 3A is an example output of a sensor configured to detect a hemodynamic property of a human.
Figure 3B:
FIG. 3B is an example output generated based on an output of a sensor configured to detect a hemodynamic property of a human.

To illustrate such sensor operations, FIG. 3A is an example detected ECG voltage waveform 310a detected from the voltage between two electrodes in contact with respective portions of a body by a sensor that could be included and/or operated as part of a system or method as described herein. The example ECG voltage waveform 310a corresponds to a series of heartbeats exhibiting an increase in heart rate. FIG. 3B shows an example estimated heart rate 310b determined based on the ECG voltage waveform 310a. Such an estimated heart rate could be determined by determining the timing of repeated features of the ECG voltage waveform 310a (e.g., QRS waves, periods of time when the ECG voltage waveform 310a exceeds a specified threshold) and calculating the rate of such repeated features (e.g., by dividing a number of features detected within a specified period of time by the duration of the specified period of time, by calculating the time interval between pairs of neighboring detected features), or by some other method. Other health states or related determined variables could be determined from a detected ECG waveform (e.g., a pulse length variability, a QRS wave amplitude variability, a presence of features indicating torsades de pointes, fibrillation, arrest, or some other health state of a heart) or from some other detected property of a body (e.g., a blood pressure, a Galvanic skin response).

Figure 3C:
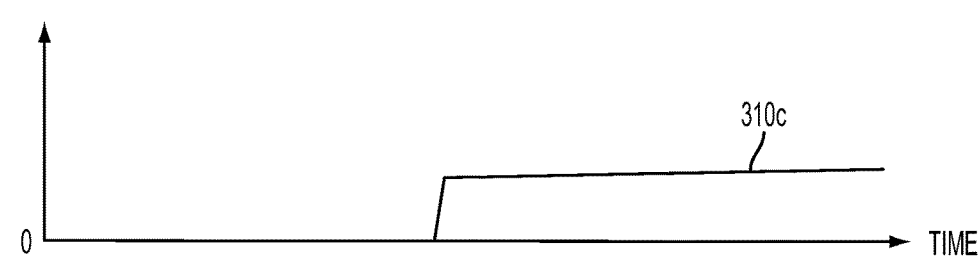
FIG. 3C is an example timing diagram of operation of a sensor configured to detect a hemodynamic property of a human.

The timing of operation of a first sensor could be based on a detected and/or determined health state or other information related to a body. As an example, FIG. 3C shows the timing of a period of operation 310c of a sensor based on the determined estimated heart rate 310b. In this example, the determination that the estimated heart rate 310b has increased above a set threshold (e.g., indicating increased stress, physical effort, or some other health state or condition) causes the sensor to operate to detect some hemodynamic property (e.g., a flow rate of blood in a portion of subsurface vasculature) during a subsequent period of time (indicated by 310c). In some examples, this could include operating the sensor to perform a single measurement; alternatively, the sensor could be operated to perform a plurality of measurements. In some examples, the subsequent period of time could have a specified duration; additionally or alternatively, the sensor could be operated during a period of time whose duration is specified or determined by some other method (e.g., to operate until a detected hemodynamic property has reached a maximum or exhibited some other behavior, to operate until the estimated heart rate 310b decreases below a specified threshold).

Figure 3D:
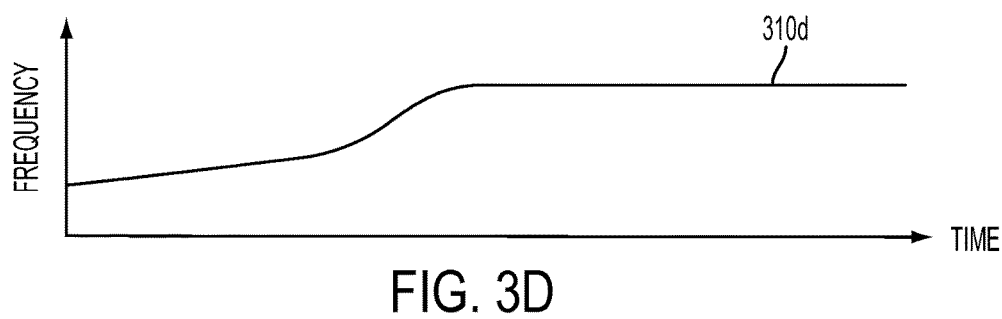
FIG. 3D is an example timing diagram of operation of a sensor configured to detect a hemodynamic property of a human.

Additionally or alternatively, operational parameters of a sensor (e.g., controlled filter cutoff frequencies) could be controlled based on a value of one or more hemodynamic properties, health states, or other properties of a body detected using a second sensor. For example, FIG. 3D shows a controlled bandpass filter center frequency 310d (e.g., the center frequency of a bandpass filter and/or amplifier of a dynamic laser speckle sensor, a Doppler ultrasonography sensor, or some other type of sensor). The values of the controlled center frequency 310d is based on the determined estimated heart rate 310b. In this example, the controlled center frequency 310d is determined for a particular point in time based on a lookup table, formula, algorithm, or other method that generates center frequencies 310d based on the determined estimated heart rate 310b for the particular point in time.

Note that the configurations and operations of sensors as described herein are meant as non-limiting examples of operation of a first sensor (e.g., controlling the timing of operation of the first sensor, controlling one or more operational parameters of the first sensor) based on one or more hemodynamic properties or other physiological properties detected using a second sensor. Such operations and/or configurations could be applied to improve a measurement of a hemodynamic property detected using the first sensor, to increase an SNR of an output of the first sensor, to reduce an overall power consumption of the first sensor, to optimize a noise characteristic of an output of the first sensor, to remove an unwanted signal component of the first sensor, or to provide some other outcome according to an application.

III. EXAMPLE WEARABLE DEVICES

Wearable devices as described herein can be configured to be mounted to an external body surface of a wearer and to enable a variety of applications and functions including the detection of hemodynamic properties (e.g., a flow rate of blood, a blood oxygenation, a blood volume in a particular portion of vasculature, a blood pressure, a blood cell velocity, a electrocardiographic (ECG) signal) or other physiological properties of one or more portions of the body of the wearer (e.g., of one or more portions of subsurface vasculature beneath the external body surface). A first sensor of a wearable device could be operated to detect a hemodynamic property of a first portion of subsurface vasculature based on a hemodynamic property of the body of the wearer (e.g., a hemodynamic property of a second portion of subsurface vasculature, a hemodynamic property of the first portion of subsurface vasculature) detected using a second sensor, as described elsewhere herein. Such wearable devices could enable a variety of applications, including measuring hemodynamic properties or other physiological information about a wearer, indicating such measured information or other information to the wearer (e.g., using a vibrator, a screen, a beeper), or other functions.

Figure 4:
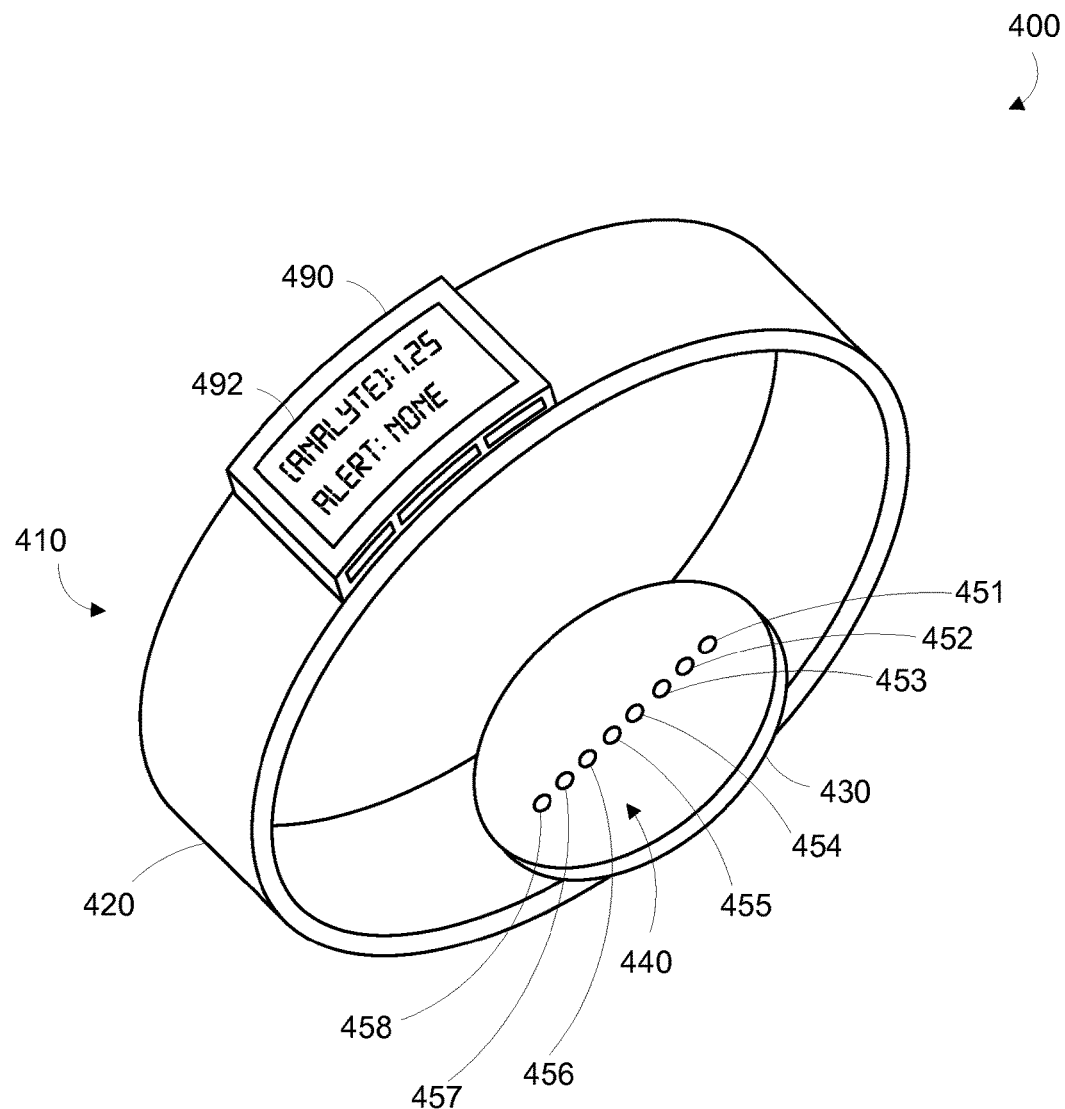
FIG. 4 is a perspective view of an example wearable device.

A wearable device 400 (illustrated in FIG. 4) can be configured to detect a plurality of hemodynamic properties (e.g., of portions of subsurface vasculature proximate the device 400) or other physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature or other targets or elements of the body of the wearer are easily observable, the qualification of which will depend on the type of detection system used. The device may be placed in close proximity to the skin or tissue. A mount 410, such as a belt, wristband, ankle band, etc. can be provided to mount the device at, on or in proximity to the body surface. The mount 410 may prevent the wearable device from moving relative to the body to reduce measurement error and noise. In one example, shown in FIG. 4, the mount 410, may take the form of a strap or band 420 that can be worn around a part of the body. Further, the mount 410 may be an adhesive substrate for adhering the wearable device 400 to the body of a wearer.

A housing 430 is disposed on the mount 410 such that it can be positioned on the body. A contact surface 440 of the housing 430 is intended to be mounted facing to the external body surface. The housing 430 may include sensors 451, 452, 453, 454, 455, 456, 457, 458 for detecting one or more hemodynamic properties of the wearer (e.g., hemodynamic properties of respective portions of subsurface vasculature). The housing 430 could be configured to be water-resistant and/or water-proof. That is, the housing 430 could be configured to include sealants, adhesives, gaskets, welds, transparent windows, apertures, press-fitted seams, and/or other joints such that the housing 430 was resistant to water entering an internal volume or volumes of the housing 430 when the housing 430 is exposed to water. The housing 430 could further be water-proof, i.e., resistant to water entering an internal volume or volumes of the housing 430 when the housing 430 is submerged in water. For example, the housing 430 could be water-proof to a depth of 1 meter, i.e., configured to resist water entering an internal volume or volumes of the housing 430 when the housing 430 is submerged to a depth of 1 meter.

The sensors 451-458 could include similar or dissimilar sensors. In one example, the sensors 451-458 could all be the same type of sensor (e.g., photoplethysmographic sensors configured to optically detect a volume of blood in respective portions of subsurface vasculature or other portions of tissue). In another example, the sensor 451-458 could include a plurality of different types of sensors.

The sensors 451-458 could detect similar or different hemodynamic properties by similar or different means. In an example, a first sensor 451 and a second 452 sensor could be a dynamic laser speckle sensor and a Doppler ultrasonography probe, respectively, configured to measure a blood flow rate in respective portions of subsurface vasculature. In another example, the first 451 and second 452 sensors could be a dynamic laser speckle sensor and a tonometer, respectively, configured to measure a blood flow rate and a blood volume, respectively, in the same portion of subsurface vasculature.

The sensors 451-458 could include a variety of types of sensors configured in a variety of ways to detect a variety of different hemodynamic properties according to an application. Sensors 451-458 could be configured to be in electrical, thermal, mechanical, fluidic, chemical, or some other form of contact or access with tissues of a body. This could include a sensor having one or more electrodes or probes having a specified electrical, thermal, or other resistance and configured to allow a flow of heat energy, electrical current, or some other energy through the electrodes or probes. For example, a sensor could include one or more thermal probes configured to allow a temperature of tissue in contact with the thermal probe(s) to be detected and/or for heat energy to be provided and/or removed from tissue in contact with the thermal probe(s). In some examples, a sensor could include two or more electrodes configured to allow a voltage between two or more respective portions of tissue in contact with the electrodes to be measured, to allow a current through the two or more electrodes to be measured, to allow a current and/or voltage to be provided to the portions of tissue, or to allow some other electrical interaction with tissue. For example, two or more electrodes could be configured to provide one or more electrocardiographic, tissue impedance, Galvanic skin potential, Galvanic skin resistance, or other electrical properties of a body to be detected.

A sensor could include one or more mechanical probes configured to detect a force and/or displacement of tissue in contact with the mechanical probe(s) and/or to transduce acoustical (e.g., ultrasonic) vibrations or energy into tissue. For example, a sensor could include a tonometer configured to detect a blood pressure, a blood volume, or some other property of subsurface vasculature beneath a portion of skin with which a mechanical probe or other element of the tonometer is in contact. In another example, a sensor could include one or more ultrasonic transducers configured to emit ultrasonic pulses or other acoustical energies into tissue and/or to receive ultrasonic pulses or other acoustical energies from tissue in contact with the one or more ultrasonic transducers. For example, a sensor could include a Doppler ultrasonography probe configured to transmit pulses and/or continuous waves of ultrasound energy into tissue (e.g., into a portion of subsurface vasculature, via intervening skin or other tissue) and to receive pulses and/or continuous waves of ultrasound energy from the tissue. One or more properties (e.g., a frequency shift relative to a frequency of ultrasound energy emitted by the sensor, a time delay and/or amplitude of a received pulse relative to an emitted pulse) of the received ultrasound energy could be used to determine a velocity of blood or other fluids in the tissue, to detect the location of tissues and/or boundaries between tissues, or to detect some other hemodynamic or other property of a body that includes the tissue.

Sensors could be configured to emit energy toward/into portions of tissue (e.g., portions of subsurface vasculature) and/or to receive energy emitted from portions of tissue to allow detection of hemodynamic or other properties of a body. Sensors could be configured to emit and/or receive light (e.g., visible, infrared, or ultraviolet light), electromagnetic radiation, acoustical vibrations (e.g., pulses of ultrasound), electrical fields, magnetic fields, or some other directed energy or energy field(s). In some examples, energy (e.g., light at an excitation wavelength of a fluorophore in tissue or blood, light at an absorption wavelength of red blood cells) could be emitted into a tissue, and energy responsively emitted from the tissue (e.g., light at an emission wavelength of an excited fluorophore, light reflected, scattered, refracted, or otherwise interacted with by blood or other tissue) could be detected and used to determine hemodynamic or other properties of a body. In such examples, one or more properties or features of an excitation spectrum, an absorption spectrum, an emission spectrum, a scattering spectrum, or some other optical property of tissues (e.g., of blood within a portion of subsurface vasculature) could be detected at one or more points in time to allow detection of hemodynamic or other properties of a body.

Optical sensors configured to emit light into/toward and/or to receive light emitted from a portion of subsurface vasculature could be configured in a variety of ways to detect a variety of properties of received light and/or to emit light having one or more specified and/or controlled properties. Such sensors could be configured to emit light in a beam having a round, linear, or other cross-sectional shape or to emit light to illuminate a broad region of a body. The direction of a beam of illumination emitted by a sensor could be fixed or controllable (e.g., by the operation of galvanometers or other actuators to control mirrors, lenses, or other optics of the sensor and/or to control a location or orientation of a sensor). Emitted light could be coherent, non-coherent, and/or could have a specified coherence length. Emitted light could be substantially monochromatic (e.g., emitted by a laser) or could otherwise have a specified wavelength and/or spectral profile. Further, properties of emitted light (e.g., wavelength, amplitude, polarization, coherence length, direction, beam width or shape) could be changed over time (e.g., a tunable laser of a sensor could be operated to emit light at a first specified wavelength at a first point in time and to emit light at a second specified wavelength at a second point in time). Further, optical sensors could be configured to detect an amplitude, wavelength, direction of polarization, degree of polarization, spectral content, relative phase, or other properties at one or more points in time and further to detect such properties in light emitted from multiple portions of a body (e.g., from multiple directions relative to the sensor, e.g., the sensor could include a camera).

In some examples, the body of a wearer could include artificial or other contrast agents (e.g., fluorophores, fluorescent nanodiamonds, chromophores, acoustic particles, magnetic particles) functionalized or otherwise configured to enable the detection of an analyte and/or of one or more properties of the body of the wearer using the sensors 451-458. For example, a contrast agent including a fluorophore could be configured to selectively bind to an analyte of interest in the blood of the wearer, and a sensor (e.g., one or more of 451-458) could be operated to determine to presence, location, binding state, or other properties of the contrast agent in the blood. Other contrast agents, properties of the body of the wearer, and configurations and methods of operation of the wearable device 400 are anticipated.

The configuration and/or operation of one or more of the sensors 451-458 could be related to a value of one or more operational parameters of the one or more sensors. Such operational parameters could include a gain (e.g., of an amplifier), a sampling rate, an integration interval, an exposure time, an attenuation factor, a filter coefficient or cutoff frequency of a filter, a selection of one or more filters from a set of filters in a switched filter bank, an operational mode (e.g., a selection between a pulsed mode for interrogation/illumination of a portion of subsurface vasculature and a continuous mode for interrogation of the portion of subsurface vasculature), or some other property of the configuration and/or operation of the one or more sensors. In some examples, such operational parameters could include parameters describing illumination or other energy used to illuminate, excite, or otherwise interact with a target tissue or other elements of a body. For example, operational parameters could include an amplitude, a wavelength, a spectral content, a coherence length, a pulse rate, a pulse duty cycle, a pulse frequency, a waveform, a degree of polarization, a direction of polarization, a beam width, a beam shape, a beam direction, a beam dispersion, or some other property of light emitted from one or more sensors.

Additionally or alternatively, one or more sensors (e.g., one or more of 451-458) of the wearable device 400 could be configured to detect alignment of a target (e.g. to detect the location of a portion of subsurface vasculature relative to one or more of the sensors 451-458) within the body of the wearer. The one or more of the sensors 451-458 could be configured to detect a hemodynamic property of the wearer and/or a target therein when the target has a specified disposition (e.g., location, orientation) relative to the one or more sensors (i.e., when the target is aligned with a particular one of the sensors). The operation of the one or more sensors to detect the hemodynamic property of the wearer and/or target could be performed in response to a determination that the target is aligned with the one or more sensors. Additionally or alternatively, operation of the one or more sensors to detect the hemodynamic property of the wearer and/or target could be related to the detected alignment. For example, a mapping or other calculation performed to determine a value of a detected hemodynamic property based on a measurement generated by the one or more sensors could be based on a determined and/or detected alignment of the target; e.g., an amplitude of a generated measurement could be normalized based on a detected alignment of the target to correct for effects of proximity between the target and the one or more sensors on measurements generated by the one or more sensors.

The wearable device 400 may also include a user interface 490 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 490 may include a display 492 where a visual indication of the alert or recommendation may be displayed. The display 492 may further be configured to provide an indication of the measured alignment and/or to indicate an adjustment which could be made by the wearer to align a target with the wearable device.

Note that the sensors 451-458 are disposed as a linear array. This could be advantageous in certain applications. For example, applications wherein alignment of a wearable device and/or components thereof is more sensitive to motion of the wearable device in one direction relative to a target than in a perpendicular direction (e.g., when the target is a long object, e.g., a portion of subsurface vasculature). Other applications wherein a linear array of sensors and/or light emitters could be advantageous include applications wherein adjustment of and/or motion between the target and the wearable device is largely constrained to a single direction/degree of freedom (e.g., when the wearable device is mounted to a protruding element of a wearer's anatomy (e.g., a wrist, and ankle, a limb)). However, many applications are anticipated wherein an array of two or more alignment- or other property-sensing sensors and/or light emitters are arranged in 2-dimensional patterns (e.g., rectangular, hexagonal, triangular, or other regularly or irregularly spaced grids, tessellations, or other patterns). Such 2-dimensional arrays of sensors could be further configured and/or operated to detect information about a target and/or about a wearer. For example, a 2-dimensional array of sensors and/or light emitters could be operated to detect a pattern, size, or other information about subsurface vasculature, nerves, or other anatomical or physiological elements of a wearer.

Further, individual sensors in an array of sensors could be discrete sensors (e.g., sensors composed of individual discrete photodetectors, photodiodes, LEDs, thermistors, micro-cameras, or other discrete components and/or sensors) could be part of a single chip, multi-chip module, lithographed element, or other composite element or device. Further, an array of sensors could include a combination of discrete sensor components and multi-sensor and/or multi-light-emitter integrated components. For example, an array of sensors and/or light emitters could include a single-chip array of VCSELs, a linear or planar CCD array, an array of PZT or other acoustic and/or piezoelectric transducers, or some other element that includes multiple sensors. The sensors in an array of sensors could be substantially identical, or could include two or more types of sensors. Some or all of the sensors in an array of sensors could be configured and/or operated to detect hemodynamic properties (e.g., of portions of subsurface vasculature); further, some or all of the sensors could be configured and/or operated to detect other information about a wearer.

Note that example devices herein are configured to be mounted to a wrist of a wearer. However, the embodiments described herein could be applied to other body parts (e.g., an ankle, a thigh, a chest, a forehead, a thigh, a finger), or to detect hemodynamic properties or other properties in other environments. For example, embodiments described herein could be applied to detect one or more properties in a target environment (e.g., a natural environment, an environment of an industrial, pharmaceutical, or water treatment process).

Wearable devices and other embodiments as described herein can include a variety of components configured in a variety of ways. Devices described herein could include electronics including a variety of different components configured in a variety of ways to enable applications of the wearable device. The electronics could include controllers, amplifiers, switches, display drivers, touch sensors, wireless communications chipsets (e.g., Bluetooth radios or other radio transceivers and associated baseband circuitry to enable wireless communications between the wearable device and some other system(s)), or other components. The electronics could include a controller configured to operate one or more sensors and/or components of sensors to detect one or more hemodynamic or other properties of a body based on hemodynamic properties detected using the one or more sensors or using some other sensor(s). The controller could include a processor configured to execute computer-readable instructions (e.g., program instructions stored in data storage of the wearable device) to enable applications of the wearable device. The electronics can include additional or alternative components according to an application of the wearable device.

Wearable devices as described herein could include one or more user interfaces. A user interface could include a display configured to present an image to a wearer and to detect one or more finger presses of a wearer on the interface. The controller or some other component(s) of the electronics could operate the user interface to provide information to a wearer or other user of the device and to enable the wearer or other user to affect the operation of the wearable device, to determine some property of the wearable device and/or of the wearer of the wearable device (e.g., a hemodynamic property of a portion of subsurface vasculature and/or a health state of a wearer of the wearable device), or to provide some other functionality or application to the wearer and/or user. As one example, the wearer could press an indicated region of the user interface to indicate that the wearable device should begin logging detected medical information about the wearer. Other indicated information, changes in operation of the wearable device, or other functions and applications of the user interface are anticipated.

Note that the embodiments illustrated in the Figures are illustrative examples and not meant to be limiting. Alternative embodiments, including more or fewer components in alternative configurations are anticipated. A wearable device could include multiple housings or other such assemblies each containing some set of components to enable applications of such a wearable device. For example, a wearable device could include a first housing within which are disposed sensors configured to detect hemodynamic properties of a wearer (e.g., of portions of subsurface vasculature of the wearer) and a second housing containing a user interface and electronics configured to operate the sensors and to present information to and receive commands from a user of the wearable device. A wearable device could be configured to perform a variety of functions and to enable a variety of applications. Wearable devices could be configured to operate in concert with other devices or systems; for example, wearable devices could include a wireless communication interface configured to transmit data indicative of one or more properties of the body of a wearer of the wearable device. Other embodiments, operations, configurations, and applications of a wearable device as described herein are anticipated.

Figure 5A:
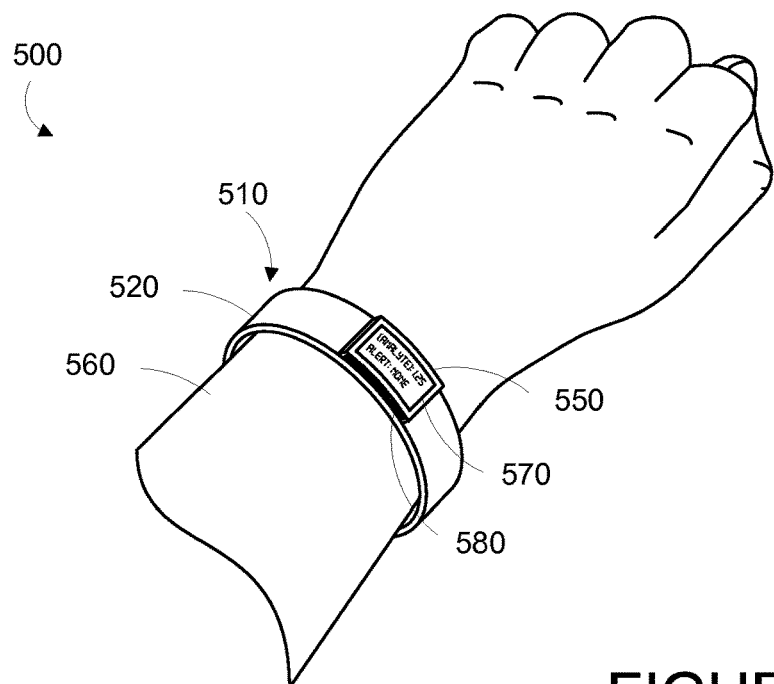
FIG. 5A is a perspective top view of an example wrist-mounted device, when mounted on a wearer's wrist.
Figure 5B:
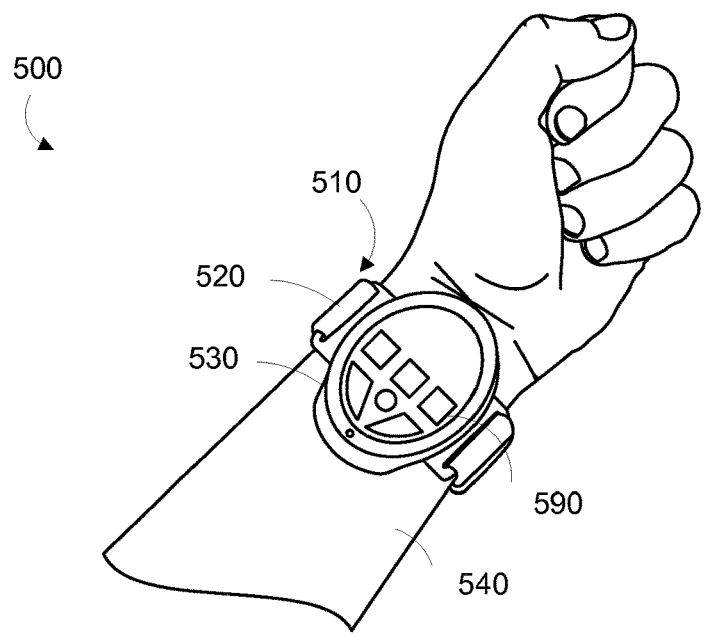
FIG. 5B is a perspective bottom view of the example wrist-mounted device shown in FIG. 5A, when mounted on a wearer's wrist.

In some examples, the wearable device is provided as a wrist-mounted device, as shown in FIGS. 5A and 5B. The wrist-mounted device may be mounted to the wrist of a living subject with a wristband or cuff, similar to a watch or bracelet. As shown in FIGS. 5A and 5B, the wrist mounted device 500 may include a mount 510 in the form of a wristband 520, a housing 530 containing a data collection system and positioned on the anterior side 540 of the wearer's wrist, and a user interface 550 positioned on the posterior side 560 of the wearer's wrist. The wearer of the device may receive, via the user interface 550, one or more recommendations or alerts generated either from a remote server or other remote computing device, or alerts from the measurement platform. Such a configuration may be perceived as natural for the wearer of the device in that it is common for the posterior side 560 of the wrist to be observed, such as the act of checking a wrist-watch. Accordingly, the wearer may easily view a display 570 on the user interface. Further, the housing 530 may be located on the anterior side 540 of the wearer's wrist where the subsurface vasculature or other elements of the body of the wearer may be readily observable. However, other configurations are contemplated.

The display 570 may be configured to display a visual indication of the alert or recommendation and/or an indication of the measured alignment of a target relative to the wearable device 500. Further, the user interface 550 may include one or more buttons 580 for accepting inputs from the wearer. For example, the buttons 580 may be configured to change the text or other information visible on the display 570. As shown in FIG. 5B, housing 530 may also include one or more buttons 590 for accepting inputs from the wearer. The buttons 590 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

FIG. 6 is a simplified schematic of a system including one or more wearable devices 600. The one or more wearable devices 600 may be configured to transmit data via a communication interface 610 over one or more communication networks 620 to a remote server 630. In one embodiment, the communication interface 610 includes a wireless transceiver for sending and receiving communications to and from the server 630. In further embodiments, the communication interface 610 may include any means for the transfer of data, including both wired and wireless communications. For example, the communication interface may include a universal serial bus (USB) interface or a secure digital (SD) card interface. Communication networks 620 may be any one of may be one of: a plain old telephone service (POTS) network, a cellular network, a fiber network and a data network. The server 630 may include any type of remote computing device or remote cloud computing network. Further, communication network 620 may include one or more intermediaries, including, for example wherein the wearable device 600 transmits data to a mobile phone or other personal computing device, which in turn transmits the data to the server 630.

In some examples, multiple wearable devices 600 could be configured to detect multiple hemodynamic or other properties of a single wearer. For example, the single wearer could wear or otherwise operate two or more wearable devices 600 to measure respective hemodynamic properties from respective two or more portions of the body of the wearer (e.g., respective portions of subsurface vasculature of the wearer). In such examples, a first sensor in a first wearable device worn by the wearer could be operated based on a hemodynamic property (or other physiological property) of the wearer detected by a second sensor in a second wearable device worn by the wearer. Information about the hemodynamic property detected by the second sensor could be transferred to the first wearable device (e.g., to enable operation of the first sensor based on the hemodynamic property) via the communication network 620, via a direct wireless link (e.g., a Bluetooth radio link) between the first and second wearable devices, via a cable or other physical connection between the first and second wearable devices, or by some other means.

In addition to receiving communications from the wearable device 600, such as collected hemodynamic properties (e.g., of portion(s) of subsurface vasculature of a wearer) or other collected physiological properties and data regarding health state as input by the user and/or one or more properties of a wearer detected using a sensor disposed in the wearable device 600, the server may also be configured to gather and/or receive either from the wearable device 600 or from some other source, information regarding a wearer's overall medical history, environmental factors and geographical data. For example, a user account may be established on the server for every wearer that contains the wearer's medical history. Moreover, in some examples, the server 630 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the hemodynamic property data and the indicated health state of the user. From this information, the server may be configured to derive an indication of the effectiveness of the drug or treatment. For example, if a drug is intended to treat nausea and the wearer of the device does not indicate that they are experiencing nausea after beginning a course of treatment with the drug, the server may be configured to derive an indication that the drug is effective for that wearer. In another example, a wearable device may be configured to measure blood pressure. If a wearer is prescribed a drug intended to treat hypertension, but the server receives data from the wearable device indicating that the wearer's blood pressure has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected hemodynamic property data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and hemodynamic properties, collected from his or her device may only be used for generating an individual baseline and recommendations in response to collection and comparison of his or her own data and may not be used in generating a population baseline or for use in population correlation studies.

IV. EXAMPLE ELECTRONICS

Figure 7:
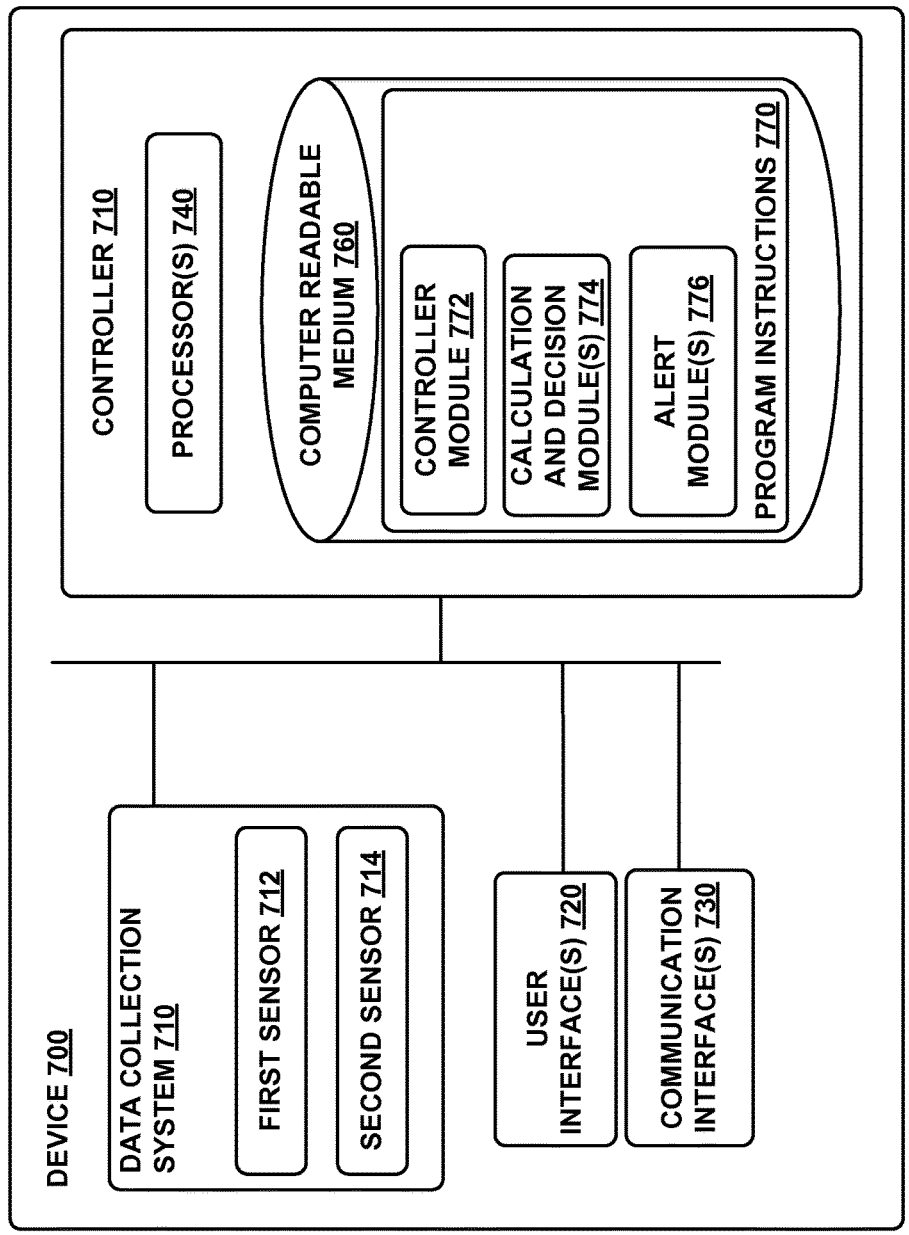
FIG. 7 is a functional block diagram of an example device.

FIG. 7 is a simplified block diagram illustrating the components of a device 700, according to an example embodiment. Device 700 may take the form of or be similar to one of the wearable devices 100, 400, 500 shown in FIGS. 1, 4, and 5A-B. However, device 700 may also take other forms, such as an ankle, waist, or chest-mounted device. Device 700 could also take the form of a device that is not configured to be mounted to a body. For example, device 700 could take the form of a handheld device configured to be maintained in proximity to an environment of interest (e.g., a body part, a biological sample container, a volume of a water treatment system) by a user or operator of the device 700 or by a frame or other supporting structure. Device 700 also could take other forms.

In particular, FIG. 7 shows an example of a device 700 having a data collection system 710 that includes two sensors 712, 714, a user interface 720, communication interface 730 for transmitting data to a remote system, and a controller 710. The components of the device 700 may be disposed on a mount or on some other structure for mounting the device to enable stable detection of one or more properties (e.g., hemodynamic properties) of an environment of interest (e.g., of a body of a wearer of the device 700), for example, mounting to an external body surface where one or more portions of subsurface vasculature or other anatomical elements are readily observable.

Controller 710 may be provided as a computing device that includes one or more processors 740. The one or more processors 740 can be configured to execute computer-readable program instructions 770 that are stored in the computer readable data storage 760 and that are executable to provide the functionality of a device 700 described herein.

The computer readable medium 760 may include or take the form of one or more non-transitory, computer-readable storage media that can be read or accessed by at least one processor 740. The one or more computer-readable storage media can include volatile and/or non-volatile storage components, such as optical, magnetic, organic or other memory or disc storage, which can be integrated in whole or in part with at least one of the one or more processors 740. In some embodiments, the computer readable medium 760 can be implemented using a single physical device (e.g., one optical, magnetic, organic or other memory or disc storage unit), while in other embodiments, the computer readable medium 760 can be implemented using two or more physical devices.

Sensors 712, 714 could include any components configured to detect hemodynamic properties and/or some other information about a body of a wearer (e.g., about one or more portions of subsurface vasculature) as described elsewhere herein. Sensors 712, 714 could be configured to detect a variety of properties of a wearer's heart, a wearer's blood, one or more portions of subsurface or other vasculature of the wearer, blood within one or more portions of subsurface or other vasculature of the wearer, or some other information about the cardiovascular system of the wearer. Sensors 712, 714 could be configured to detect such properties at/in different portions of subsurface vasculature (e.g., two portions of vasculature in a wrist, upstream and downstream portions of an artery, vein, or other blood vessel) or in the same portion of subsurface vasculature (e.g., a flow rate and a volume of blood in a single portion of subsurface vasculature). For example, hemodynamic properties of the radial and ulnar artery of the wrist could be detected. In another example, a hemodynamic property of vasculature in a wrist and in vasculature of the head or torso (e.g., behind the ear) could be detected. Further, electrocardiograms or other hemodynamic properties of the wearer could be detected at one or more locations.

The sensors 712, 714 could include temperature sensors, energy sensors, electromagnetic sensors, light sensors, chemical sensors, acoustical sensors, infrared sensors, ultraviolet sensors, tonometers, electrocardiogram electrodes, tissue impedance electrodes, or other types of sensors. The sensors 712, 714 could include photodetectors (e.g., light detectors, color detectors, polarity detectors, infrared detectors, ultraviolet detectors, cameras). In some examples, one or more of the sensors 712, 714 could include energy emitters (e.g., light emitters, heaters, acoustical transducers, current sources, voltage sources) configured to enable detection of some hemodynamic property of a body of a wearer (e.g., of a portion of subsurface vasculature of the wearer) by illuminating, heating, injecting a current into, applying a voltage to, or otherwise introducing an energy to the one or more portions of the body of the wearer. For example, the sensors 712, 714 could include one or more Doppler ultrasonography probes. In some examples, the sensors 712, 714 could include active optical sensors configured to illuminate a portion of subsurface vasculature and/or blood therein and the detect light responsively emitted from the portion of subsurface vasculature. Such sensors could include laser Doppler flowmeters, dynamic laser speckle sensors, photoplethysmographic sensors, fluorescence imagers, or some other active and/or passive optical sensors.

The configuration and/or operation of one or more of the sensors 712, 714 could be related to a value of one or more operational parameters of the sensors 712, 714. Such operational parameters could include a gain (e.g., of an amplifier), a sampling rate, an integration interval, an exposure time, an attenuation factor, a filter coefficient or cutoff frequency of a filter, a selection of one or more filters from a set of filters in a switched filter bank, an operational mode (e.g., a selection between a pulsed mode for interrogation/illumination of a portion of subsurface vasculature and a continuous mode for interrogation of the portion of subsurface vasculature), or some other property of the configuration and/or operation of the sensors 712, 714. In some examples, such operational parameters could include parameters describing illumination or other energy used to illuminate, excite, or otherwise interact with a target tissue or other elements of a body. For example, operational parameters could include an amplitude, a wavelength, a spectral content, a coherence length, a pulse rate, a pulse duty cycle, a pulse frequency, a waveform, a degree of polarization, a direction of polarization, a beam width, a beam shape, a beam direction, a beam dispersion, or some other property of light emitted from one or more of the sensors 712, 714.

The program instructions 770 stored on the computer readable medium 760 may include instructions to perform any of the methods described herein. For instance, in the illustrated embodiment, program instructions 770 include a controller module 772, calculation and decision module 774 and an alert module 776.

Calculation and decision module 774 may include instructions for operating the sensors 712, 714 and analyzing data generated by the sensors 712, 714 to determine one or more hemodynamic properties or other information (e.g., health states) of a body of a wearer of the device 700, such as flow rate of blood in a portion of subsurface vasculature at a plurality of points in time. Calculation and decision module 774 can additionally include instructions for analyzing the data to determine if a medical condition or other specified condition is indicated, or other analytical processes relating to the environment proximate to the device 700. In particular, the calculation and decision module 774 may include instructions for operating the first sensor 712 based on a hemodynamic property or other information detected and/or determined using the second sensor 714 as described elsewhere herein. These instructions could be executed at each of a set of preset measurement times.

The controller module 772 can also include instructions for operating a user interface 720. For example, controller module 772 may include instructions for displaying data collected by the data collection system 710 and analyzed by the calculation and decision module 774, or for displaying one or more alerts generated by the alert module 776. Controller module 772 may include instructions for displaying data related to a detected hemodynamic property of one or more portions of subsurface vasculature or some other detected and/or determined health state of a wearer. Further, controller module 772 may include instructions to execute certain functions based on inputs accepted by the user interface 720, such as inputs accepted by one or more buttons disposed on the user interface.

Communication platform 730 may also be operated by instructions within the controller module 772, such as instructions for sending and/or receiving information via a wireless antenna, which may be disposed on or in the device 700. The communication interface 730 can optionally include one or more oscillators, mixers, frequency injectors, etc. to modulate and/or demodulate information on a carrier frequency to be transmitted and/or received by the antenna. In some examples, the device 700 is configured to indicate an output from the processor by modulating an impedance of the antenna in a manner that is perceivable by a remote server or other remote computing device.

The program instructions of the calculation and decision module 774 may, in some examples, be stored in a computer-readable medium and executed by a processor located external to the device 700. For example, the device 700 could be configured to collect certain data regarding hemodynamic properties from the user and then transmit the data to a remote server, which may include a mobile device, a personal computer, the cloud, or any other remote system, for further processing.

The computer readable medium 760 may further contain other data or information, such as medical and health history of a user of the device 700, that may be useful in determining whether a medical condition or some other specified condition is indicated. Further, the computer readable medium 760 may contain data corresponding to certain physiological parameter baselines, above or below which a medical condition is indicated. The baselines may be pre-stored on the computer readable medium 760, may be transmitted from a remote source, such as a remote server, or may be generated by the calculation and decision module 774 itself. The calculation and decision module 774 may include instructions for generating individual baselines for the user of the device 700 based on data collected over a certain number of measurement periods. Baselines may also be generated by a remote server and transmitted to the device 700 via communication interface 730. The calculation and decision module 774 may also, upon determining that a medical or other emergency condition is indicated, generate one or more recommendations for the user of the device 700 based, at least in part, on consultation of a clinical protocol. Such recommendations may alternatively be generated by the remote server and transmitted to the device 700.

In some examples, the collected hemodynamic property data, baseline profiles, health state information input by device users and generated recommendations and clinical protocols may additionally be input to a cloud network and be made available for download by a user's physician. Trend and other analyses may also be performed on the collected data, such as hemodynamic property data and health state information, in the cloud computing network and be made available for download by physicians or clinicians.

Further, hemodynamic property and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 774 that a medical or other specified condition is indicated, the alert module 776 may generate an alert via the user interface 720. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication.

V. EXAMPLE METHODS

Figure 8:
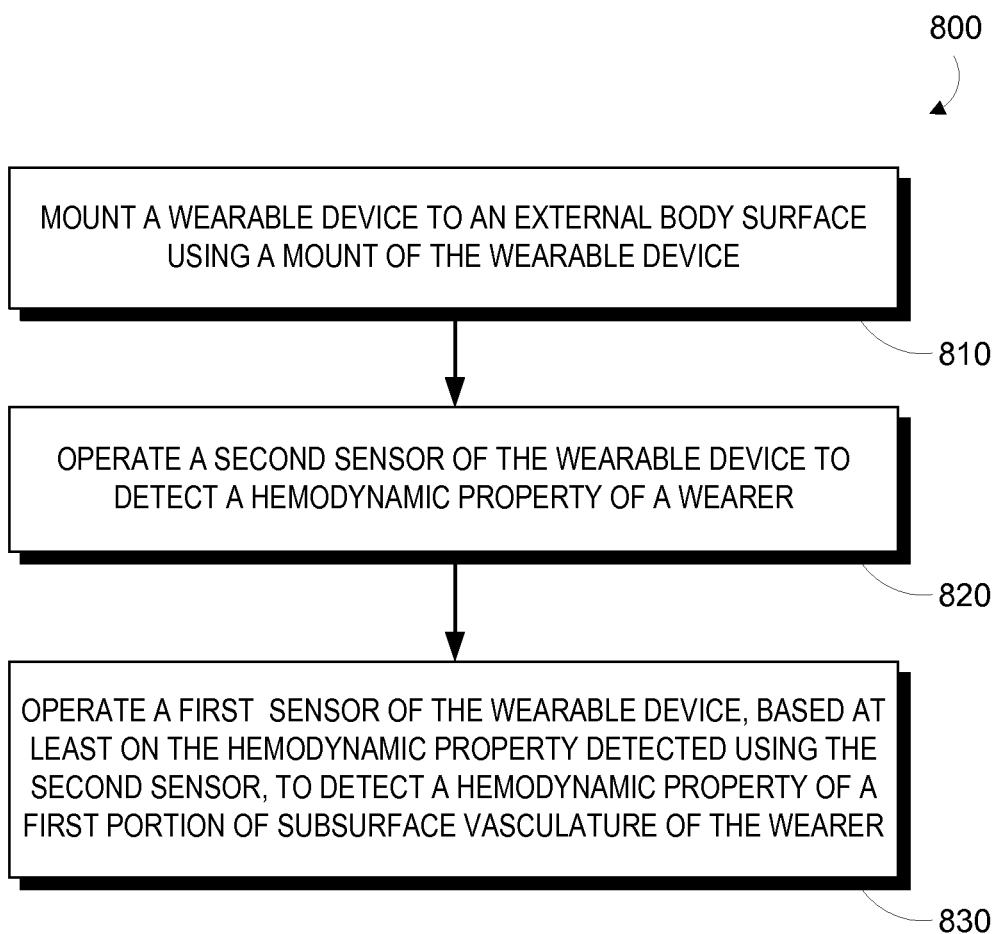
FIG. 8 is a flowchart of an example method.

FIG. 8 is a flowchart of a method 800 for operating a wearable device. The operated wearable device includes: (i) a first sensor configured to detect a hemodynamic property of a first portion of subsurface vasculature of a wearer when the first sensor is located proximate to the first portion of subsurface vasculature; (ii) a second sensor configured to detect a hemodynamic property of a wearer when the second sensor is disposed proximate to an external body surface of the wearer; (iii) a mount configured to mount the first sensor to an external body surface proximate to the first portion of subsurface vasculature; and (iv) a controller operably coupled to the first and second sensors. The sensors 712, 714 could include temperature sensors, energy sensors, electromagnetic sensors, light sensors, chemical sensors, acoustical sensors, infrared sensors, ultraviolet sensors, tonometers, electrocardiogram electrodes, tissue impedance electrodes, or other types of sensors. In some examples, one or more of the sensors 712, 714 could include energy emitters (e.g., light emitters, heaters, acoustical transducers, current sources, voltage sources) configured to enable detection of some hemodynamic property of a body of a wearer (e.g., of a portion of subsurface vasculature of the wearer) by illuminating, heating, injecting a current into, applying a voltage to, or otherwise introducing an energy to the one or more portions of the body of the wearer. In some examples, the sensors 712, 714 could include active optical sensors configured to illuminate a portion of subsurface vasculature and/or blood therein and the detect light responsively emitted from the portion of subsurface vasculature. Such sensors could include laser Doppler flowmeters, dynamic laser speckle sensors, photoplethysmographic sensors, fluorescence imagers, or some other active and/or passive optical sensors.

The method 800 includes mounting the wearable device to an external body surface using the mount (810). In some examples, the wearable device could be configured to be mounted to a wrist of a wearer (e.g., the embodiments illustrated in FIGS. 1, 4, and 5A-B) such that the first sensor can be operated to detect a hemodynamic property of the first portion of subsurface vasculature proximate to and/or within the wrist of the wearer. In some examples, the mount includes an adhesive, and mounting the wearable device to the external body surface (810) includes activating, applying, and/or exposing the adhesive and adhering the wearable device to the external body surface. In some examples, the wearable device could be configured such that the second sensor is also mounted to the external body surface such that the second sensor can be operated to detect a hemodynamic property of a second portion of subsurface vasculature, of the first portion of subsurface vasculature, or of some other element(s) of the body of the wearer via the external body surface.

The method 800 also includes operating the second sensor of the wearable device to detect a hemodynamic property of the wearer (820). This could include operating the second sensor in any of a variety of ways to detect any of a variety of hemodynamic or other physiological properties as described elsewhere herein. Hemodynamic properties detected by the second sensor could include properties of a wearer's heart, a wearer's blood, one or more portions of subsurface or other vasculature (e.g., the first portion of subsurface vasculature, a portion of subsurface vasculature upstream from the first portion of subsurface vasculature, some other portion of subsurface vasculature) of the wearer, blood within one or more portions of subsurface or other vasculature of the wearer, or some other information about the cardiovascular system of the wearer.

The method 800 also includes operating the first sensor of the wearable device, based at least on the hemodynamic property detected using the second sensor, to detect a hemodynamic property of the first portion of subsurface vasculature of the wearer (830). This could include operating the first sensor at a specified point in time and/or during a specified period of time to detect a hemodynamic of the first portion of subsurface vasculature. Such a specified point in time and/or period of time could be determined based on a timing of one or more events (e.g., a maximum flow rate of blood in a portion of vasculature, a QRS wave in an ECG) detected using the second sensor and/or a phase of a repeated process (e.g., a pulse phase of the heartbeat of the wearer) determined using the second sensor. In some examples, this (830) could include controlling an operational parameters of the first sensor. Such operational parameters could include a gain (e.g., of an amplifier), a sampling rate, an integration interval, an exposure time, an attenuation factor, a filter coefficient or cutoff frequency of a filter, a selection of one or more filters from a set of filters in a switched filter bank, an operational mode (e.g., a selection between a pulsed mode for interrogation/illumination of a portion of subsurface vasculature and a continuous mode for interrogation of the portion of subsurface vasculature), or some other property of the configuration and/or operation of the first sensor. In some examples, such operational parameters could include parameters describing illumination or other energy used to illuminate, excite, or otherwise interact with a target tissue or other elements of a body. For example, operational parameters could include an amplitude, a wavelength, a spectral content, a coherence length, a pulse rate, a pulse duty cycle, a pulse frequency, a waveform, a degree of polarization, a direction of polarization, a beam width, a beam shape, a beam direction, a beam dispersion, or some other property of light emitted from a first sensor.

The method 800 for operating a wearable device could include additional steps relating to detection of hemodynamic properties or other physiological information about a wearer and/or tissues of the wearer (e.g., portions of subsurface vasculature of the wearer) and/or other functions of the wearable device. In some examples, the wearable device could include multiple separate housings or other elements separately containing the first and second sensors, and the method 800 could include transmitting (e.g., wirelessly transmitting, transmitting via a Bluetooth wireless link, transmitting via a cable, transmitting via the internet or some other network) information indicative of the hemodynamic property detected using the second sensor from a housing or other element containing the second sensor to a housing or other element containing the first sensor. In some examples, the method 800 could include determining a health state of the wearer based on a hemodynamic property detected using the first and/or second sensors. In some examples, the method 800 could include indicating a detected hemodynamic property to a user via a user interface of the wearable device and/or indicating such information to a remote system (e.g., to a physician's computer, via a wireless or other communications link).

The example method 800 illustrated in FIG. 8 is meant as an illustrative, non-limiting example. Additional or alternative elements of the method and additional or alternative components of the wearable device are anticipated, as will be obvious to one skilled in the art.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A wearable device, comprising:
   a first sensor, wherein the first sensor is configured to detect a first hemodynamic property of a first portion of subsurface vasculature of a wearer of the wearable device, wherein the first sensor comprises a filter;
   a second sensor configured to detect a second hemodynamic property of a second portion of subsurface vasculature of the wearer of the wearable device, wherein the first portion of subsurface vasculature and the second portion of subsurface vasculature are part of the same blood vessel, wherein the second sensor is a different type of sensor than the first sensor;
   a mount configured to mount the first sensor and the second sensor to an external body surface of the wearer such that the first sensor is proximate to the first portion of subsurface vasculature; and
   a controller operably coupled to the first and second sensors, wherein the controller comprises a computing device programmed to perform operations comprising:
      detecting, using the second sensor, the second hemodynamic property relating to the wearer;
      determining, based on the detected second hemodynamic property, a filter parameter for the filter of the first sensor;
      detecting, using the first sensor, the first hemodynamic property relating to the first portion of subsurface vasculature, wherein using the first sensor to detect the first hemodynamic property of the first portion of subsurface vasculature comprises operating the first sensor with the filter configured according to the determined filter parameter; and
      providing an output indicative of the detected first hemodynamic property.

2. The wearable device of claim 1, wherein the first and second portions of subsurface vasculature overlap, and wherein the mount is further configured to mount the second sensor to the external body surface proximate to the first portion of subsurface vasculature.

3. The wearable device of claim 1, wherein providing an output indicative of the detected first hemodynamic property comprises transmitting data indicative of the first hemodynamic property to a server.

4. The wearable device of claim 1, wherein at least one of the first sensor or second sensor comprises a Doppler ultrasonography probe.

5. The wearable device of claim 1, wherein at least one of the first sensor or second sensor comprises a tonometer.

6. The wearable device of claim 1, wherein at least one of the first sensor or second sensor comprises a photoplethysmographic sensor.

7. The wearable device of claim 1, wherein at least one of the first sensor or second sensor comprises a dynamic laser speckle sensor.

8. The wearable device of claim 1, wherein the filter parameter controls a frequency response of the filter.

9. The wearable device of claim 1, wherein the filter parameter selects the filter from a set of filters.

10. The wearable device of claim 1, wherein the filter comprises a bandpass filter.

11. The wearable device of claim 10, wherein the filter parameter comprises at least one of a cutoff frequency, a center frequency, or a bandwidth of the bandpass filter.

12. A method, comprising:
   mounting a wearable device to an external body surface of a wearer, wherein the wearable device comprises:
      a first sensor, wherein the first sensor is configured to detect a first hemodynamic property of a first portion of subsurface vasculature of the wearer, wherein the first sensor comprises a filter;
      a second sensor configured to detect a second hemodynamic property of a second portion of subsurface vasculature of the wearer, wherein the first portion of subsurface vasculature and the second portion of subsurface vasculature are part of the same blood vessel, wherein the second sensor is a different type of sensor than the first sensor;

a mount configured to mount the first sensor and the second sensor to the external body surface such that the first sensor is proximate to the first portion of subsurface vasculature; and a controller operably coupled to the first and second sensors, wherein the controller comprises a computing device;

operating, by the controller, the second sensor to detect the second hemodynamic property relating to the wearer;

determining, by the controller based on the detected second hemodynamic property, a filter parameter for the filter of the first sensor;

operating, by the controller, the first sensor with the filter configured according to the determined filter parameter to detect the first hemodynamic property relating to the first portion of subsurface vasculature; and providing an output indicative of the detected first hemodynamic property.

13. The method of claim 12, wherein the first and second portions of subsurface vasculature overlap, and wherein the mount is further configured to mount the second sensor to the external body surface proximate to the first portion of subsurface vasculature.

14. The method of claim 12, wherein providing an output indicative of the detected first hemodynamic property comprises transmitting data indicative of the first hemodynamic property to a server.

15. The method of claim 12, wherein the filter parameter controls a frequency response of the filter.

16. The method of claim 12, wherein the filter parameter selects the filter from a set of filters.

17. The method of claim 12, wherein the filter comprises a bandpass filter.

18. The method of claim 17, wherein the filter parameter comprises at least one of a cutoff frequency, a center frequency, or a bandwidth of the bandpass filter.

* * * * *